(12) United States Patent
Lehner et al.

(10) Patent No.: US 7,070,785 B2
(45) Date of Patent: Jul. 4, 2006

(54) HEAT SHOCK PROTEINS FOR USE IN ENHANCING CELLULAR FACTOR PRODUCTION

(76) Inventors: Thomas Lehner, Guy's King's & St. Thomas' Hosp. Med. Schools, 3rd Fl., New Guy's House, Guy's Hosp, London SE1 9RT (GB); Charles George Kelly, Guy's King's & St.Thomas' Hosp. Med. Schools, 28th Fl. New Guy's House, Guy's Hosp, London SE1 9RT (GB); Yufei Wang, Guy's King's & St. Thomas' Hosp. Med. Schools, 3rd Fl. New Guy's House, Guy's Hosp, London SE1 9RT (GB)

( * ) Notice: Subject to any disclaimer, the term of this patent is extended or adjusted under 35 U.S.C. 154(b) by 283 days.

(21) Appl. No.: 10/168,901

(22) PCT Filed: Dec. 21, 2000

(86) PCT No.: PCT/GB00/04957

§ 371 (c)(1),
(2), (4) Date: Sep. 23, 2002

(87) PCT Pub. No.: WO01/45738

PCT Pub. Date: Jun. 28, 2001

(65) Prior Publication Data

US 2003/0129195 A1 Jul. 10, 2003

(30) Foreign Application Priority Data

Dec. 22, 1999 (GB) ................................. 9930443.8

(51) Int. Cl.
*A61K 39/00* (2006.01)
(52) U.S. Cl. ............... 424/185.1; 424/85.1; 424/193.1; 530/300; 530/350; 530/403
(58) Field of Classification Search ................ 530/300, 530/350, 403; 424/85.1, 185.1, 193.1
See application file for complete search history.

(56) References Cited

FOREIGN PATENT DOCUMENTS

| WO | WO 97/06821 A | 2/1997 |
|---|---|---|
| WO | WO 97/45543 A | 12/1997 |
| WO | WO 97/47319 A | 12/1997 |
| WO | WO 98 34641 A | 8/1998 |

OTHER PUBLICATIONS

Chackerian et al. Induction of autoantibodies to mouse CCR5 with recombinant papillomavirus particles. Proceedings of the National Academy Science U S A. (1999) vol. 96, No. 5, pp. 2373-2783.*
Barrios et al. Mycobacterial heat-shock proteins as carrier molecules. II European Journal of Immunology (1992) vol. 22, p. 1365-1372.*
Blond-Elguindi, et al. "Affinity Panning of a Liberty of Peptides Displayed on Bacteriophages Reveals the Binding Specificity of BiP." Cell, 75, 717-728.
Ciupitu, et al. "Immunization with a Lymphocytic Choriomeningitis Virus Peptide Mixed with Heat Shock protein 70 Results in Protective Antiviral Immunity and Specific Cytotoxic T Lymphocytes." J. Exp. Med., 187, 685-691, 1998.
Cocchi, et al. "The V3 domain of the HIV-1 gp120 envelope glycoprotein is critical for chemokine-mediated blockade of infection." Nature Med., 2, 1244-1247, 1996.
Doyle, et al. "Regions Required for CD4 Binding in the External Glycoprotein gp120 of Simian Immunodeficiency Virus." J. Immunol., 69, 1256-1260, 1995.
Lehner Thomas, et al. "Heat shock proteins generate beta-chemokines which function as innate adjuvants enhancing adaptive immunity." European Journal of Immunology, vol. 30, No. 2, Feb. 2000, pp. 594-603. XP000985909.
Lehner Thomas, et al. "The role of γδ T cells in generating antiviral factors and beta-chemokines in protection against mucosal simian immunodificiency virus infection." European Journal of Immunology, vol. 30, No. 8, Aug. 2000, pp. 2245-2256. XP000985908.

(Continued)

*Primary Examiner*—Ulrike Winkler
(74) *Attorney, Agent, or Firm*—Kenneth I. Kohn; Kohn & Associates, PLLC

(57) ABSTRACT

The present invention relates to the use of heat shock proteins to enhance production of one or more chemokines by a cell. The present invention also relates to the use of a heat shock protein in the treatment or prophylaxis of an infectious disease. The present invention also relates to a peptide from an extracellular domain of CCR5 and the use of the peptide in the treatment or prophylaxis of an infectious disease.

1 Claim, 10 Drawing Sheets

OTHER PUBLICATIONS

Lehner, et al. "Induction of inhibitory antibodies to the CCR5 chemokine receptor and their complementary role in preventing SIV infection in macaques." Eur. J. Immunol., 29, 2427-2435, 1999.

Lehner, et al. "A rational basis for mucosal vaccination against HIV infection." Immunological Reviews, 170, 183-196, 1999.

Lehner, et al. "Targeted Lymph Node Immunization with Simian Immunodeficiency Virus p27 Antigen to Elicit Genital, Rectal, and Urinary Immune Responses in Nonhuman Primates." J. Immunol., 153, 1858-1868, 1994.

Lehner, et al., "Protective mucosal immunity elicited by targeted iliac lymph node immunization with a subunit SIV envelope and core vaccine in macaques." Nature Medicine, 2, 767-775, 1996.

Lehner, et al. "T- and B-cell functions and epitope expression in nonhuman primates immunized with simian immunodeficiency virus antigen by the rectal route." PNAS USA, 90, 8638-8642, 1993.

Moriuchi Hiroyuki, et al. "CD8+ T-cell-derived soluble factor(s), but not beta-chemokines RANTES, MIP-1-alpha, and MIP-1-beta, suppress HIV-1 replication in monocyte/macrophages." Proceedings of the National Academy of Sciences of the United States, vol. 93, No. 26, 1996, pp. 15341-15345. XP002166307.

Nieland, et al. "Isolation of an immunodominant viral peptide that is engogenously bound to the stress protein GP96/GRP94." PNAS USA, 93, 6135-6139, 1996.

Peng, et al. "Purification of immunogenic heat shock protein 70- peptide complexes by ADP-affinity chromatography." J. Imm. Methods, 204, 13-21, 1997.

Rucker, et al. "Regions in β-Chemokine Receptors CCR5 and CCR2b That Determine HIV-1 Cofactor Specificity." Cell, 87, 437-446, 1996.

Simmons, et al. "Potent Inhibition of HIV-1 Infectivity in Macrophages and Lymphocytes by a Novel CCR5 Antagonist." Science, 276, 276-279, 1997.

Suzue K, et al. "Adjuvant-Free HSP70 Fusion Protein System Elicits Humoral and Cellular Immue Repsonse to HIV-1." Journal of Immunology, US, The William and Wilkins Co. Baltimore, vol. 156, 1996, pp. 873-879. XP002070468.

Thole, et al. "Characterization, Sequence Determination, and Immunogenicity of a 64-Kilodalton Protein of *Mycobacterium bovis* BCG Expressed in *Escherichia coli* K-12." Infect & immune., 55, 1466-1475, 1987.

Udono, et al. "Heat Shock Protein 70-associated Peptides Elicit Specific Cancer Immunity." J. Exp. Med., 178, 1390-1396, 1993.

Verani Alessia, et al. "C-C chemokines released by lipopolysaccharide (LPS)-stimulated human macrophages suppress HIV-1 infection in both macrophages and T cells." Journal of Experimental Medicine, vol. 185, No. 5, 1997, pp. 805-816. XP002166304.

Wang Yufei, et al. "Innate function of 70-kD heat shock protein n stimulation of beta-chemokines." Journal of Human Virology, vol. 3, No. 5, Sep. 2000, p. 243. XP002166305.

Wang, et al. "Generation of CD8 suppressor factor and β chemokines, induced by xenogeneic immunization, in the prevention of simian immunodeficiency virus infection in macaques." PNAS USA, 95, 5223-5228, 1998.

Yamaguchi H, et al. "Induction of Secretion of Interleukin-8 from Human Gastric Epithelial Cells by Heat-Shock Protein 60 Homologue of Helicobacterpylori." Journal of Medical Microbiology, Harlow, GB, vol. 48, No. 10, Oct. 1999, pp. 927-933, XP000965601.

Zhu, et al. "Structural Analysis of Substrate Binding by the Molecular Chaperone DnaK." Science, 272, 1606-1614, 1996.

Zuegel Ulrich, et al. "Immune Response against heat shock proteins in infectious diseases." Immunobiology, vol. 201, No. 1, Sep. 1999, pp. 22-35. XP000995062.

Mackewicz, C.E., et al. "Non-cytolytic CD8 T-cell anti-HIV responses in primary HIV-1 infection." The Lacet, vol. 344, 1671-1673, Dec. 17, 1994.

Mehlert, A., et al. "Biochemical and antigenic characterization of the *Mycobacterium tuberculosis* 71kD antigen, a member of the 70kD heat-shock protein family." Mol. Microbial, 3, 125-130, 1989.

Young, D.B., et al. "Mycobacterial protein antigens: a compilation." Mol. Microbial., 6, 133-145, 1992.

* cited by examiner

FIG. 1

Dual protection hypothesis against HIV/SIV, cognate immunity (1 and 2) and Innate Immunity (3) by β-chemokines blocking or down modulating CCR5

FIG. 8

Binding of $^{125}$I-labelled CCR5 loop 2 peptide to *M. tuberculosis* HSP70

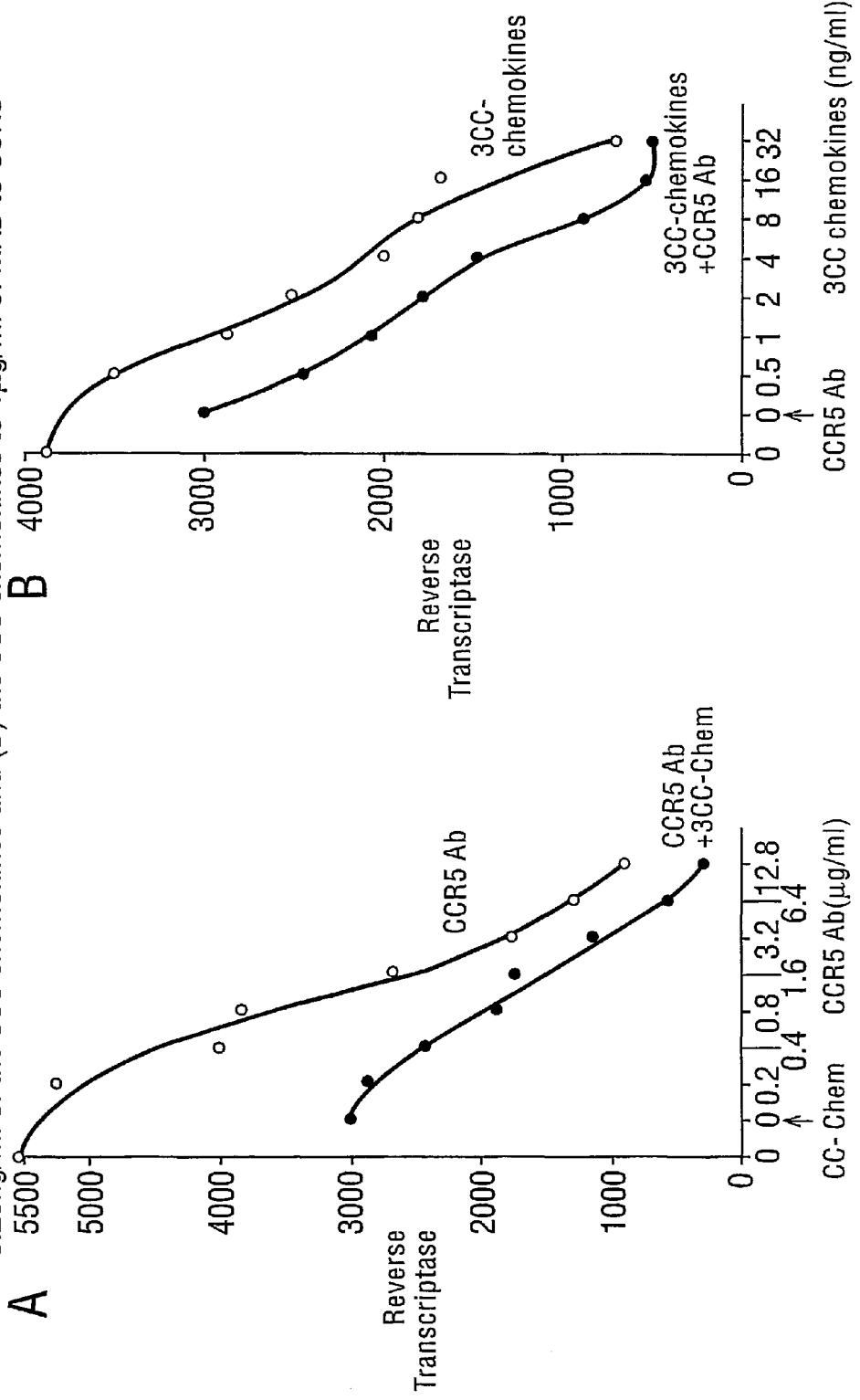
FIG. 2 The effect on HIV replication by adding increasing concentrations of (A) MAb CCR5 to 0.25ng/ml of the 3CC chemokines and (B) the 3CC chemokines to 1μg/ml of MAB to CCR5

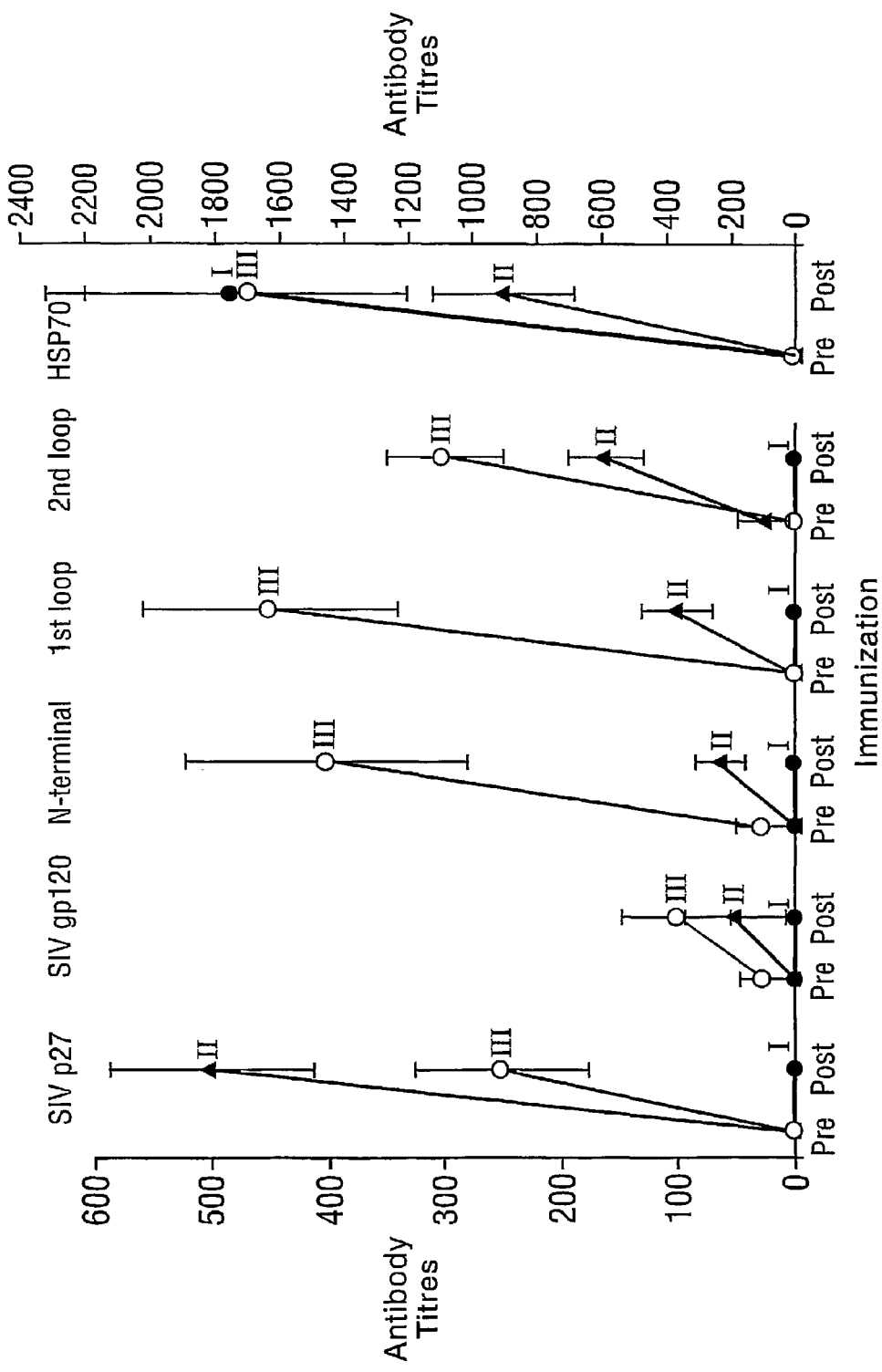
FIG. 3 Serum IgG antibodies before and after the third immunization with HSP70 (Group I), HSP70 with SIV p27 and gp120 (Group II) and the latter with the 3 CCR5 peptides (Group III)

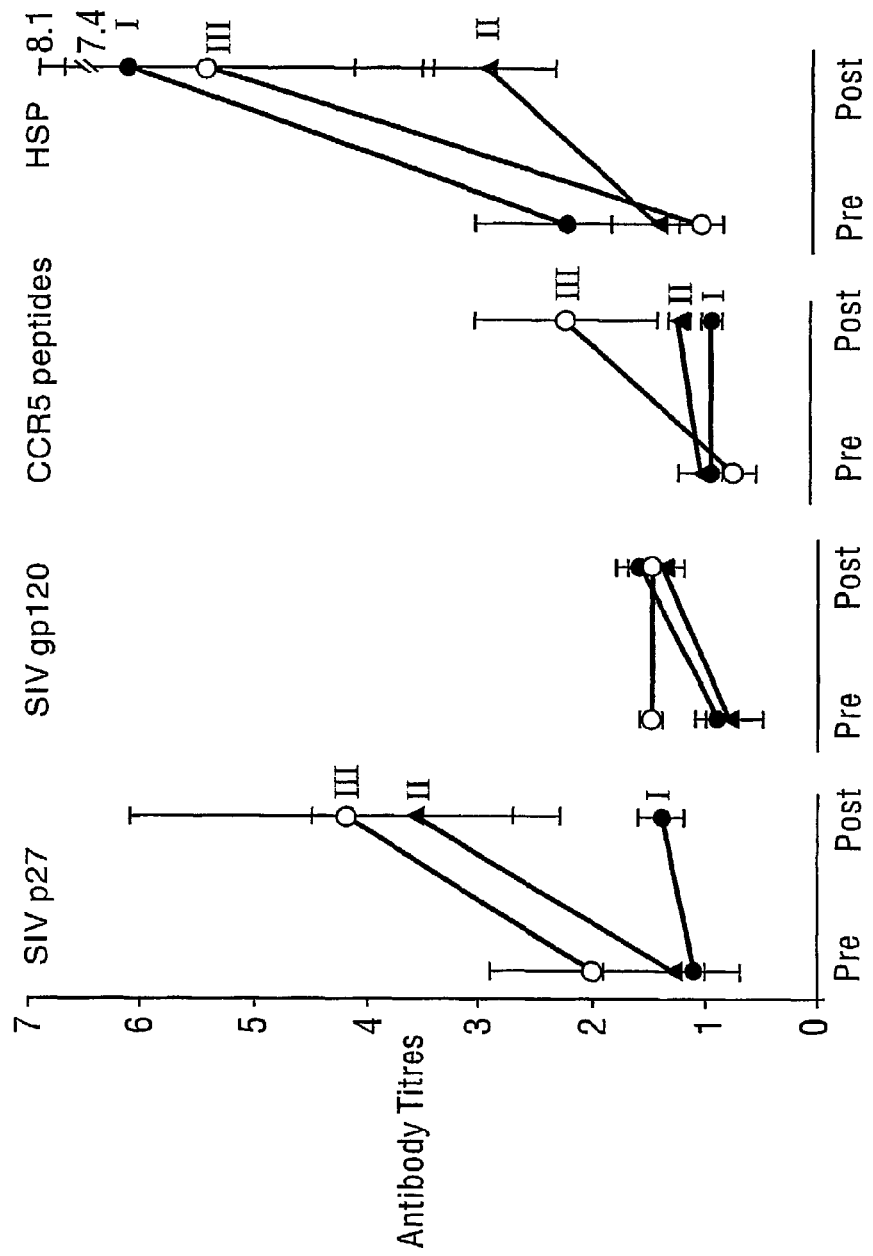
FIG. 4 T cell proliferation before and after the third immunization with HSP70 (Group I), HSP70 with SIV p27 and gp120 (Group II) and the latter with the 3 CCR5 peptides (Group III)

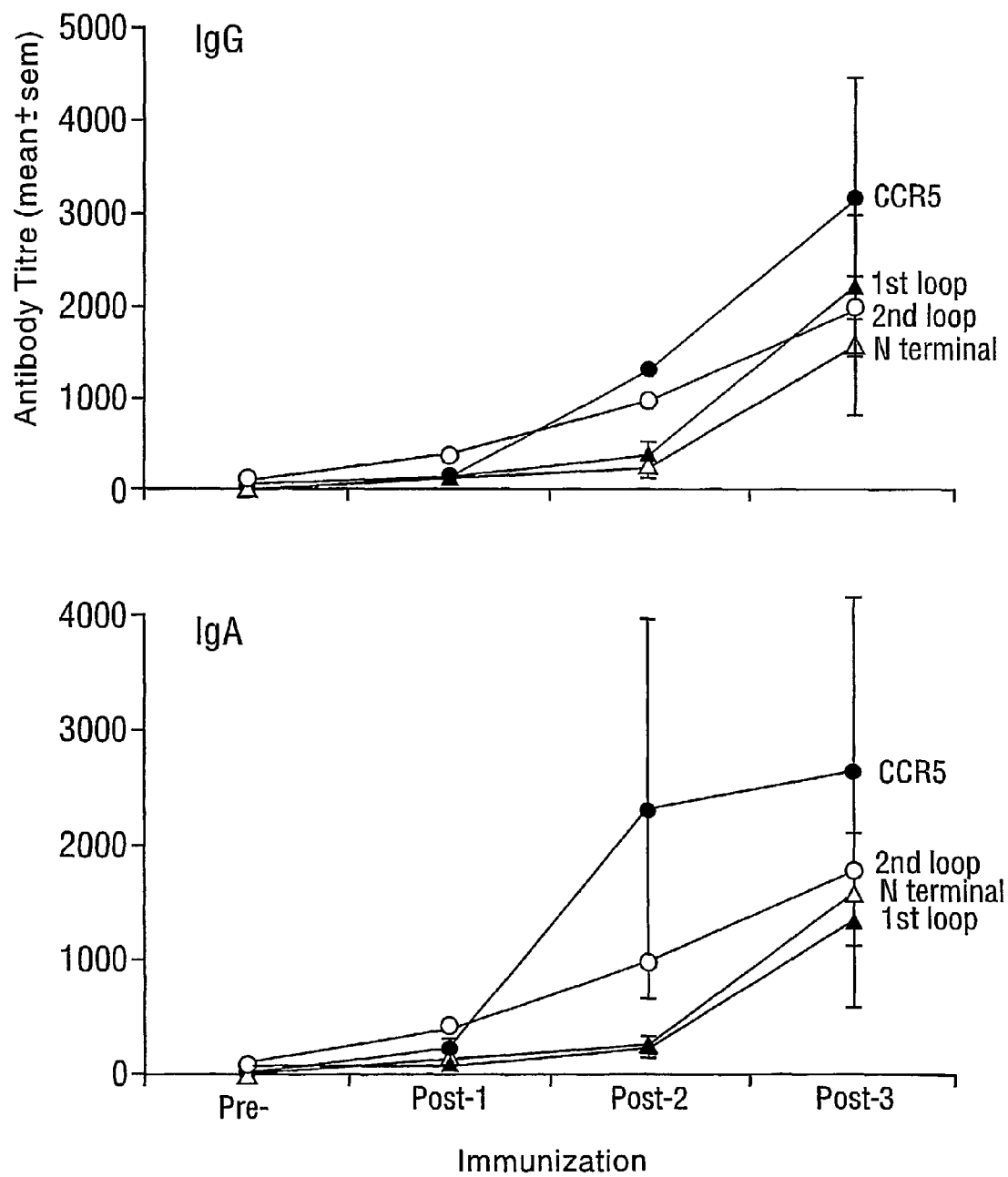
FIG. 5 Serum IgG and IgA antibodies to CCR5 or its extracellular peptides, after immunization (x3) with CCR5 or its peptides

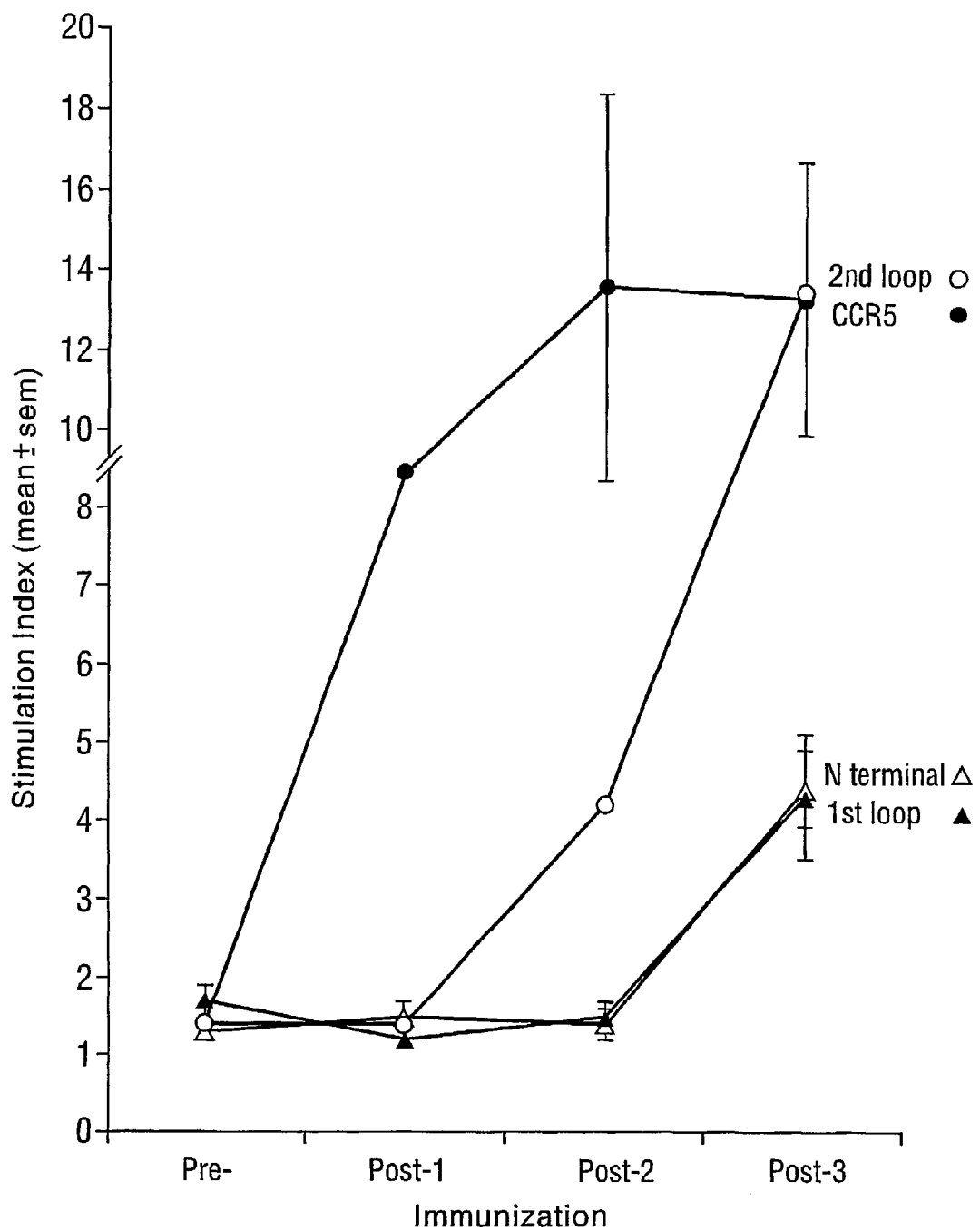
FIG. 6 T cell proliferation stimulated by CCR5 or its extracellular peptides, after immunization (x3) with CCR5 or its peptides

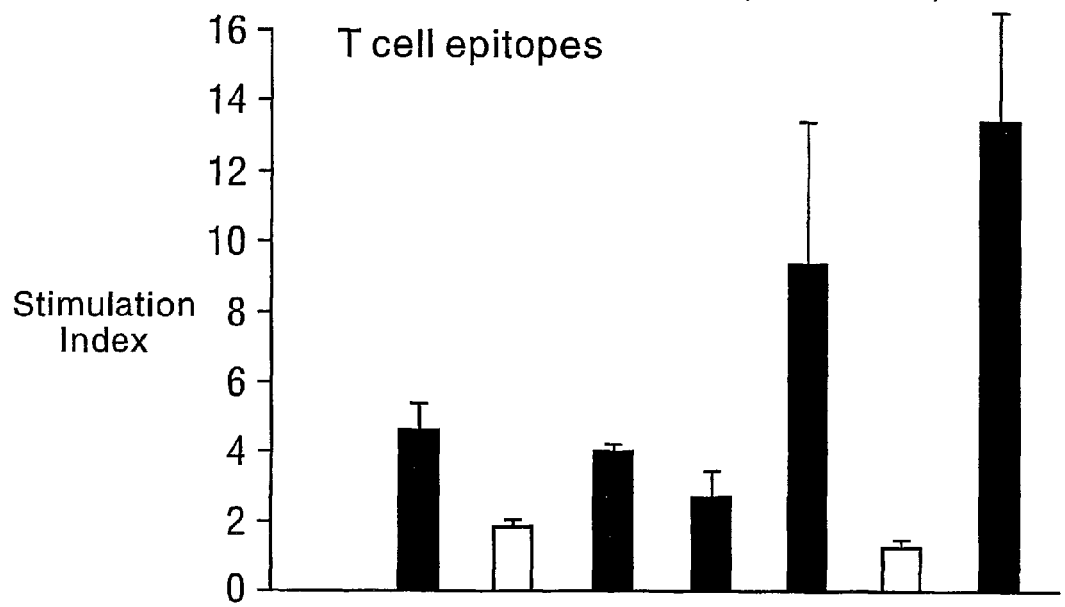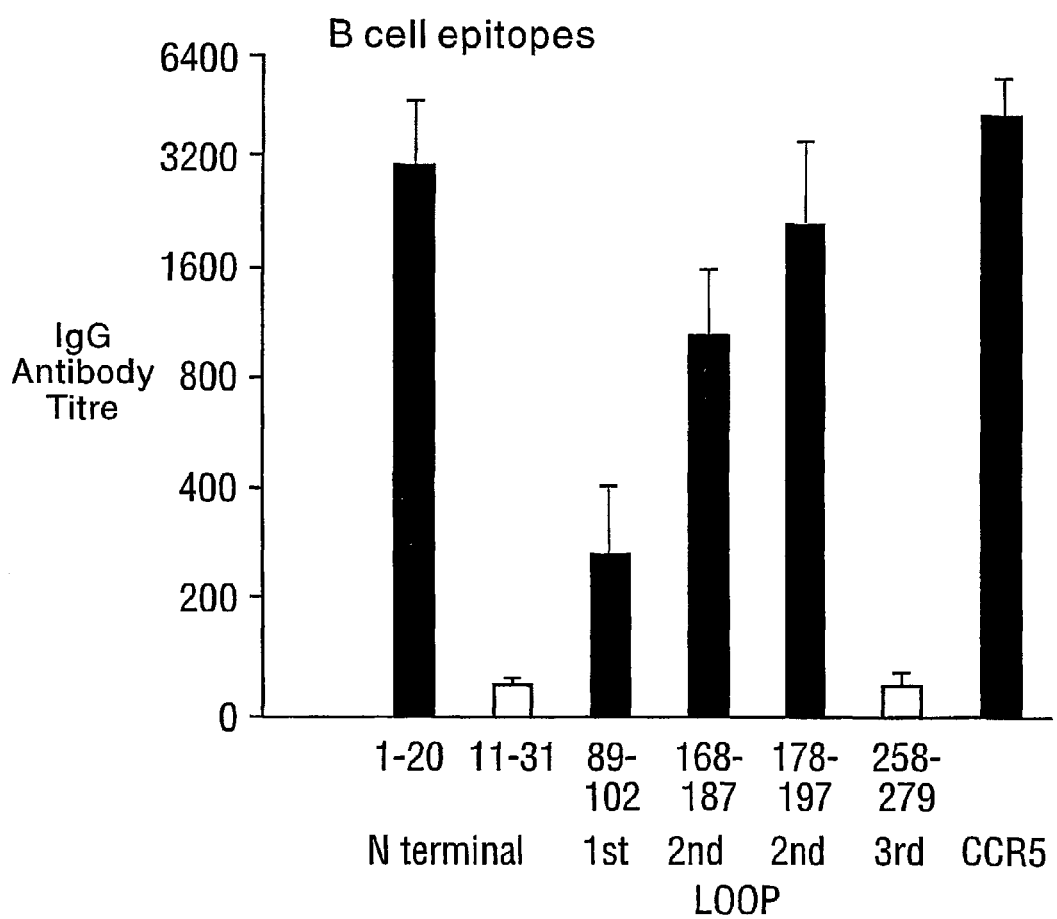
FIG. 7 T and B cell epitope mapping of extracellular domains after immunization with CCR5 (Mean + sem)

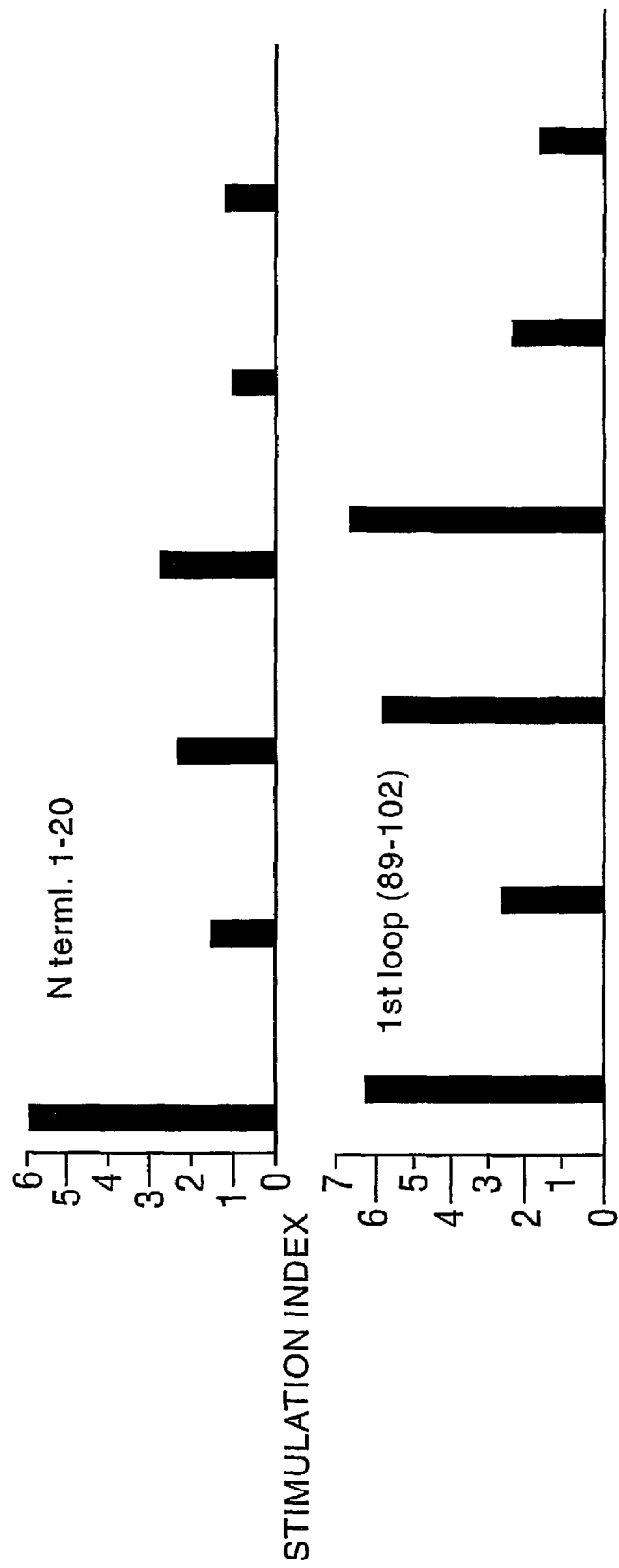
FIG. 9 T cell proliferative responses to CCR5 and its extracellular domains in PBMC, spleen and lymph nodes after immunisation of 4 macaques each with CCR5 or one of the 3 extracellular peptides

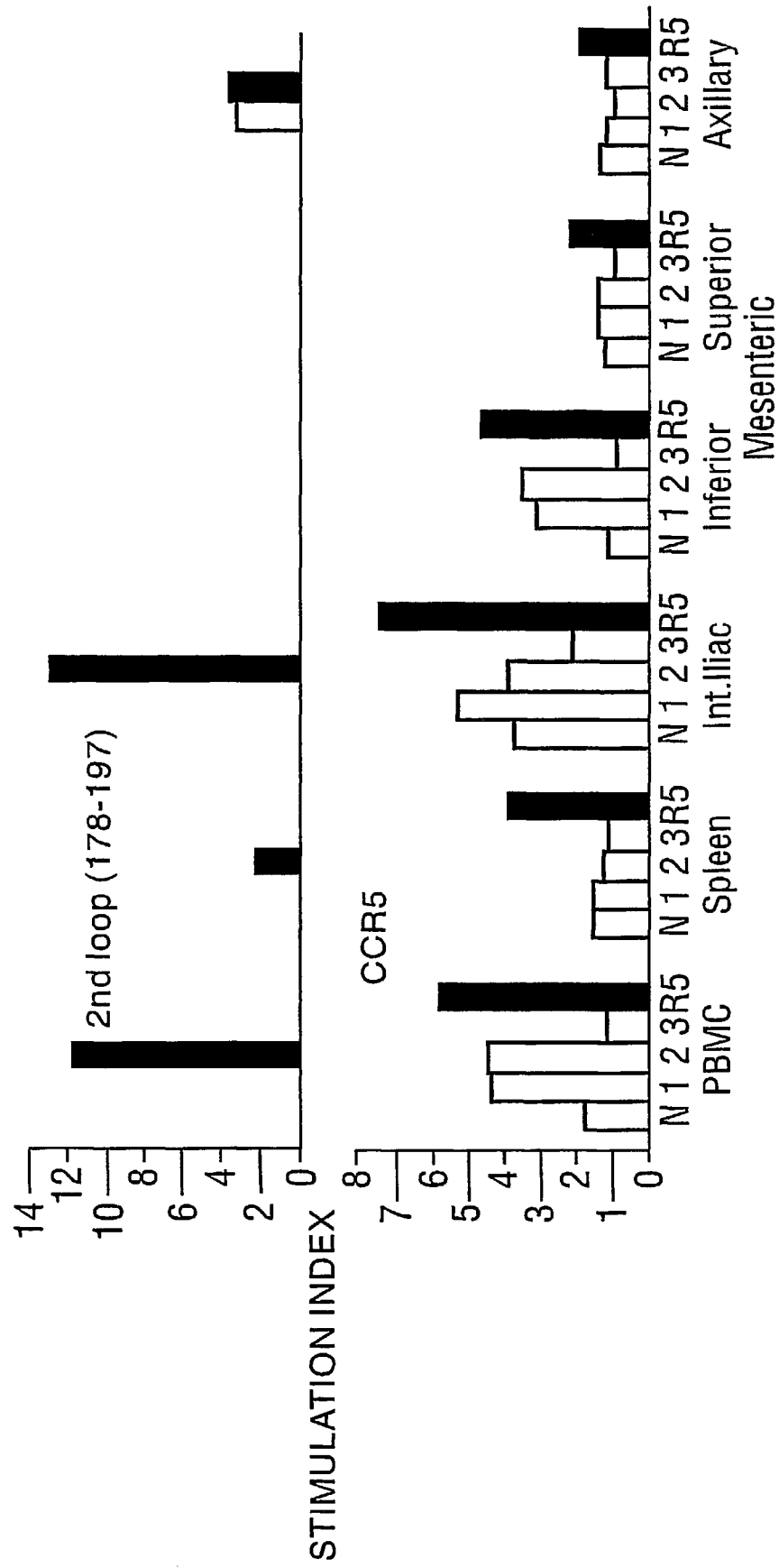
FIG. 9(CONTD.)

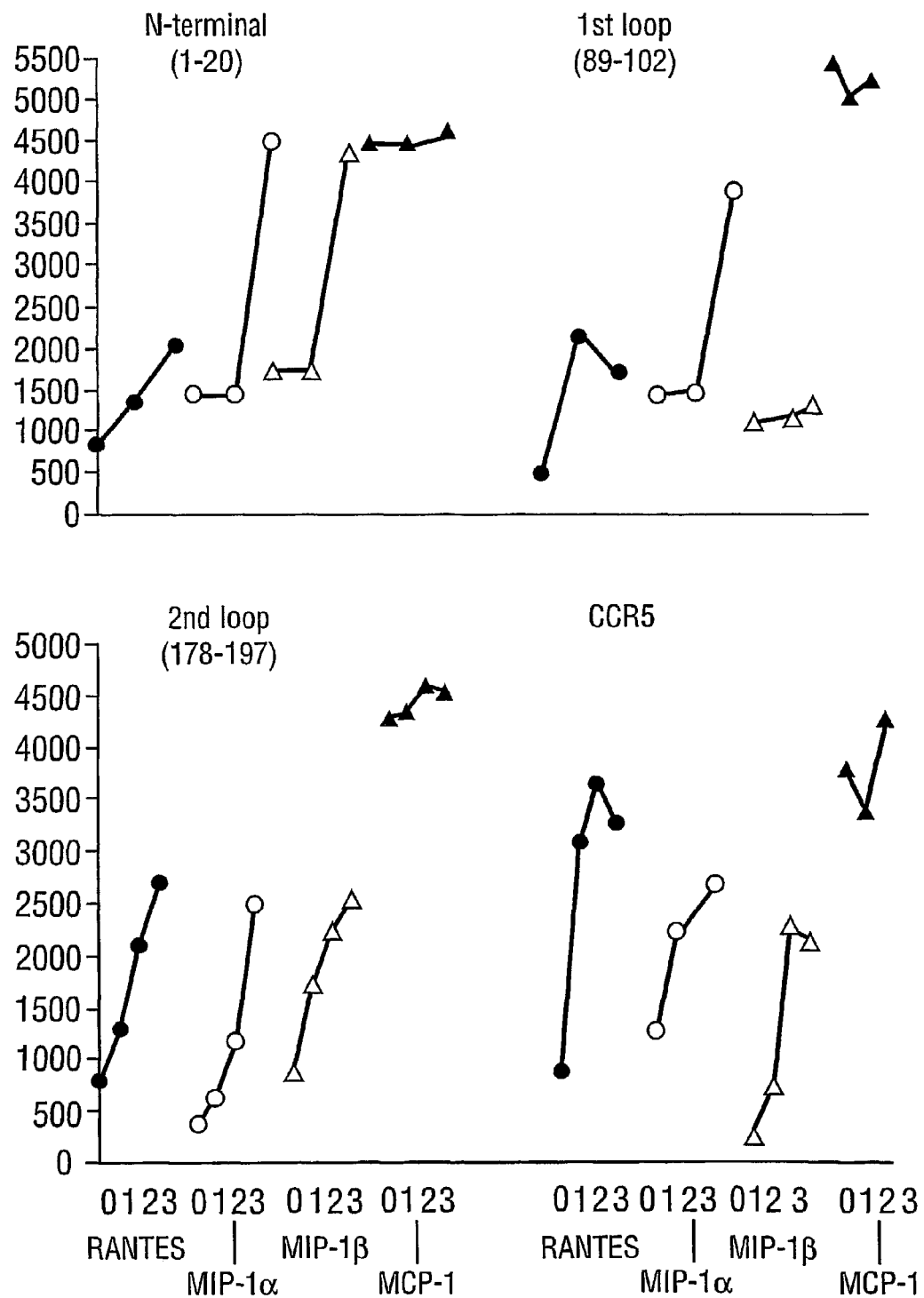
FIG. 10 Concentration of 4 β-chemokines after immunization with N-terminal (aa1-20) 1st loop (aa89-102) and 2nd loop (aa178-197) peptides or CCR5 lysate in alum, in 4 representative macaques

HEAT SHOCK PROTEINS FOR USE IN ENHANCING CELLULAR FACTOR PRODUCTION

CROSS-REFERENCE TO RELATED APPLICATIONS

This patent application is a National Phase Concerning a Filing Under 35 U.S.C. 371, claiming the benefit of priority of PCT/GB00/04957, filed Dec. 21, 2000, which claims the benefit of priority of GB Ser. No. 9930443.8, filed Dec. 22, 1999, all of which are incorporated herein by reference.

The present invention relates to the use of heat shock proteins to enhance production of one or more chemokines and/or a suppressor factor by a cell. The present invention also relates to the use of a heat shock protein in the treatment or prophylaxis of an infectious disease. The present invention also relates to a peptide from an extracellular domain of CCR5 and the use of the peptide in the treatment or prophylaxis of an infectious disease.

Heat Shock Proteins (HSP) are highly conserved and widely distributed in micro-organisms as well as mammalian cells. They have a number of important biological properties, especially as intracellular chaperones of proteins, and prevent proteins from aggregating when cells are stressed. HSP have been used as carrier molecules and adjuvants, when linked to synthetic peptides.

HSP70 and HSP96 have been non-covalently bound with tumour or virus-specific peptides and been shown to have a protective effect against the specific tumour or virus (Udono et al., J. Exp. Med., 178, 139–1396, 1993; Nieland et al., PNAS USA, 93, 6135–6139, 1996; and Ciupitu et al., J. Exp. Med., 187, 685–691, 1998). The mechanism of adjuvanicity of HSP has not been elucidated.

Chemokines are proteins that have chemoattractant and proinflammatory properties i.e. they recruit cells required for an immune response. They are produced by a variety of cell types including natural killer (NK) cells as well as antigen presenting cells such as macrophages and dendritic cells. Chemokines exert function by binding to cell surface receptors that are members of the seven transmembrane domain G protein-coupled receptors. The β-chemokines RANTES, MIP-1α and MIP-1β bind to the CCR5 receptor and attract antigen processing and presenting macrophages, dendritic cells (DC) and effector T and B cells.

A suppressor factor is a substance which is present in the culture supernatant of stimulated $CD8^+$ cells which inhibits SIV or HIV replication. The method for assaying for the suppressor factor is given herein.

CCR5 is a β-chemokine receptor and serves an important function in chemotaxis of lymphocytes, monocytes and dendritic cells. CCR5 is also the major co-receptor in most M-tropic HIV-1 infections. CCR5 is a 7-transmembrane G-protein coupled molecule expressed on TH1 and TH0 cells, $CD4^+$ CD45 RO+ memory cells, macrophages and immature dendritic cells. CCR5 is an important cell surface receptor regulating the traffic of mononuclear cells by binding β-chemokines. The receptors play an essential role in inflammatory processes and autoimmunity, and they bind RANTES, MIP-1α, MIP-1β as well as vMIP-I and II. The CCR5 cell surface molecule has acquired a central stage in HIV infection, as it functions as a major co-receptor to the CD4 glycoprotein receptor, for primary M-tropic HIV and M- and T-tropic SIV infections. Indeed many primary SIV strains use CCR5 to infect simian cells in the absence of CD4, suggesting that CCR5 and not CD4 was the primordial SIV receptor.

International patent application WO 97/06821 discloses combinations of HSP and target antigens. The nature of the binding between the two components is not precisely defined. The biological response to the components is stated as humoral or cellular but little specific data concerning the biological response is presented in the application. The application does not disclose the use of a heat shock protein to enhance the production of chemokines by a cell.

According to a first aspect of the present invention, the present invention provides the use of a heat shock protein to enhance production of one or more chemokines and/or a suppressor factor by a cell.

It has been found that by contacting a cell with a heat shock protein the production of chemokines is enhanced. Chemokines attract a variety of T cells and macrophages and T cell suppressor factors which can suppress HIV and/or SIV replication. The enhanced production of chemokines may therefore lead to the treatment or prevention of infectious diseases such as microbial infection (including viral infections) and malignant diseases.

It has also been found that by contacting a cell with a heat shock protein the production of a suppressor factor is enhanced. The suppressor factor can suppress UV and/or SIV replication. The enhanced production of a suppressor factor may therefore lead to the treatment or prevention of infectious diseases such as microbial infection (including viral infections) and malignant diseases. A suppressor factor is defined as a substance which is present in the culture supernatant of stimulated $CD8^+$ cells and which inhibits SIV or HIV replication. The method for assaying for the suppressor factor is given herein. The suppressor factor is also referred to herein as SF, CD8-SF and T cell suppressor factor.

The term "heat shock protein" as used herein refers to any protein which exhibits increased expression in a cell when the cell is subjected to a stress. Preferably the heat shock protein is derived from a mammalian cell more preferably a human cell. It is further preferred that the heat shock protein is HSP70, HSP65, HSP40, HSP27, BiP, GP96, HSP60, HSP90 or HSP96. The heat shock protein may be a modified heat shock protein, wherein the heat shock protein has been modified to provide it with advantageous characteristics such as increased resistance to degradation or to reduce the size of a heat shock protein while still maintaining its ability to enhance the production of one or more chemokines.

Heat shock proteins are commercially available. For example, HSP70 can be obtained from StressGen, Inc. and Lionex Diagnostics and Therapeutics, Braunschweig, Germany; HSP65 can be obtained from StressGen, Inc.; HSP40 can be obtained from StressGen Biotechnologies, Victoria, British Colombia. Genes encoding various heat shock proteins have been cloned and sequenced. For example, the human sequence of HSP70 has Genebank accession number M24743, mouse HSP70 has Genebank accession M35021, human HSP65 has Genebank accession number P42384 and human HSP40 has Genebank accession number D49547. Based on the known sequences of the heat shock proteins, it would be a routine matter for one skilled in the art to obtain the desired heat shock protein.

Furthermore, the preparation and purification of heat shock proteins has been described in the following references:

Young et al, Mol. Microbial., 6, 133–145, 1992; Mehlert et al, Mol. Microbial., 3, 125–130, 1989; and Thole et al, Infect & Immune., 55, 1466–1475, 1987.

The term "enhanced production of one or more chemokines" refers to the increased production of one or more chemokines by a cell when contacted with the heat shock protein. The enhanced production of the one or more chemokines may be the result of increased expression of genes encoding the chemokines, or maybe the result of the release of chemokines from the cell. It is preferred that the production of the one or more chemokines is enhanced by at least 2 fold, more preferably at least 4 fold and most preferably at least 8 fold over the level of the one or more chemokines produced by a cell which is not contacted with a heat shock protein.

The term "enhanced production of a suppressor factor" refers to the increased production of one or more suppressor factors by a cell when contacted with the heat shock protein. The enhanced production of a suppressor factor means that the suppressor factor is produced to a level sufficient to inhibit HIV or SIV infection by at least 30%, more preferably at least 50% and most preferably at least 75%.

The term "chemokine" refers to any protein that has chemoattractant and proinflammatory properties, i.e. it recruits cells required for an immune response. The chemokines are generally of relatively low molecular weight (generally less than 10,000). Chemokines are produced by a variety of cell types including endothelial cells, keratinocytes, fibroblasts, natural killer (NK) cells and antigen presenting cells such as macrophages and dendritic cells. Chemokines attract phagocytic cells and lymphocytes. Preferably the chemokines are β-chemokines. It is further preferred that the chemokines are RANTES (regulated upon activation normal T cell expressed and secreted) MIP-1α (macrophage inflammatory protein 1α) and MIP-1β (macrophage inflammatory protein 1β).

The cell may be contacted with the heat shock protein more than once. It has been found that by contacting the cell with the heat shock protein more than once, it is possible to obtain higher levels of the one or more chemokines. The present invention therefore encompasses contacting a cell with a heat shock protein once or several times in order to obtain an enhanced production of one or more chemokines and/or a suppressor factor by the cell. The term "several times" means that the cell may be contacted with the heat shock protein 2 or more times, preferably 3 to 50 times, more preferably 3 to 6 times. The interval between the repeated contacts may be from 1 day to many years depending on how long the immunological memory persists. Preferably the interval between repeated contacts is 1 month.

The use of a heat shock protein as defined in the present invention enables the enhanced production of one or more chemokines by a cell. The production of the one or more chemokines can attract a variety of T cells and macrophages, and T cell suppressor factors which can protect the cells from infectious agents such as viruses and against tumours.

Preferably the heat shock protein used in the first aspect of the present invention does not comprise a heterologous peptide. However, it will be apparent to one skilled in the art that the heat shock protein of the present invention can be used in combination with a non-linked peptide or other components such as an antibody.

The term "a heterologous peptide" refers to any peptide that in its native state does not naturally form part of a heat shock protein. A peptide is herein defined as a polymer of amino acids and does not refer to a specific length of the product; thus, peptides, oligopeptides and proteins are included within the term peptide. The term also does not refer to or exclude post-expression modifications of the protein, for example, glycosylations, acetylations and phosphorylations. Included in the definition are peptides containing one or more analogs of an amino acid (including for example, unnatural amino acids), proteins with substituted linkages, as well as other modifications known in the art, both naturally occurring and synthesised. Preferably the peptide is less that 1000 amino acid residues in length, more preferably less than 100 amino acids and length and most preferably less that 50 amino acids in length.

In an alternative embodiment of the first aspect of the present invention, it is preferred that the heat shock protein used in the present invention comprises one or more linked heterologous peptides. Preferably, the linked one or more peptides are immunogenic peptides.

The term "an immunogenic peptide" refers to any peptide that can give rise to an immunogenic response within an animal body such as a mammal e.g. a human. The immunological response may be the ability of the peptide to induce an antibody or cellular response, or to stimulate a series of immune reactions in an animal that are mediated by white blood cells including lymphocytes, neutrophils and monocytes. Preferred immunogenic peptides include those derived from viruses, bacteria, protozoa, and tumours. It is particularity preferred that the immunogenic peptide is from IV or SIV. Preferably the immunogenic peptide is gp120 or p24 from HIV.

In an alternative embodiment, it is preferably the linked one or more peptides are derived from the extracellular domains of CCR5. It is further preferred that the peptides derived from the extracellular domains of CCR5 are immunogenic peptides. It is still further preferred that the peptides are derived from the N-terminal end or the first and second extracellular loop domains of CCR5.

Preferably peptides are derived from a mammalian CCR5, more preferably human CCR5. The sequence of human CCR5 and the extracellular domains of CCR5 are described in Rucker et al., Cell, 87, 437–446, 1996.

It is particularly preferred that at least one of the one or more peptides derived from the extracellular domains of CCR5 comprise the sequence: MDYQVSSPIYDINYYT-SEPC (SEQ ID No:1): HYAAAQWDFGNTMCQ (SEQ ID No:2); CSSHFPYSQYQFWKNFQTLK (SEQ ID No:3), DINYYTSEPCQKINVKQIAAR (SEQ ID No:4), RSQKEGLHYTCSSHFPYSQY (SEQ ID No:5) or NTFQ-EFFGLNNCSSSNRLDQ (SEQ ID No:6).

It is further preferred that at least one of the peptides linked to the heat shook protein used in the present invention consist of the following sequence: MDYQVSSPIY-DINYYTSEPC SEQ ID No:1 HYAAAQWDFGNTMCQ SEQ ID No:2); CSSHFPYSQYQFWKNFQTLK (SEQ ID No:3), DINYYTSEPCQKINVKQIAAR (SEQ ID No:4), RSQKEGLHYTCSSHFPYSQY (SEQ ID No:5) or NTFQ-EFFGLNNCSSSNRLDQ (SEQ ID No:6).

It is most preferred that the peptide linked to the heat shock protein comprises at least a substantial part of the second extracellular loop of 00R5, namely at least a substantial part of NTFQEFFGLNNCSSSNRLDQ (SEQ ID No: 6). A substantial part is defined as at least 6, more preferably at least 10 contiguous amino acids.

The one or more peptides linked to the heat shock protein used in the present invention can be covalently linked or non-covalently linked to the heat shock protein. In order for the peptides to be non-covalently linked to the heat shock protein, the one or more peptides must have a hydrophobic region comprising at least 2, more preferably at least 3 and most preferably six hydrophobic residues, which can form a non-covalent link with the heat shock protein. The hydrophobic region can be at either end of the peptide or within the peptide. Preferably the heat shock protein is HSP70 and the hydrophobic region of the peptide forms a non-covalent link in a pocket present on HSP70. Preferably the hydrophobic region has the sequence motif described in Zhu et al., Science, 272, 1606–1614, 1996 or Blond-Elguindi et al., Cell, 75, 717–728.

If the one or more peptides are covalently linked to the heat shock protein, it is preferred, in order to avoid changing the conformation of the covalently linked peptide, to use a linker between the one or more peptides and the heat shock protein. Preferably the linker is glutaraldehyde or N-succinimydyl-3(2-pyridyldithio) propionate (SPDP). The use of glutaraldehyde and SDPD as linkers is well known to those skilled in the art.

According to a second aspect of the present invention the present invention provides the use of a heat shock protein which does not comprise a heterologous immunogenic protein in the manufacture of a composition for the treatment or prophylaxis of an infectious disease.

The second aspect of the present invention also provides a method of treatment or prophylaxis of an infectious disease, comprising administering to a patient in need of such treatment or prophylaxis an effective dose of a heat shock protein which does not comprise a heterologous immunogenic protein.

The heat shock protein and immunogenic protein are as defined above. The heat shock protein used in the manufacture of the composition for the treatment or prophylaxis of an infectious disease may comprise one or more non-immunogenic peptides; however, preferably the heat shock protein does not comprise a heterologous peptide. A non-immunogenic peptide is a peptide that does not give rise to an immunogenic response.

Preferably the infectious disease is a microbial infection such as a viral infection. It is particularly preferred that the infectious disease is an HIV infection.

As indicated above for the first aspect of the present invention, the one or more non-immunogenic peptides may be covalently or non-covalently linked to the heat shock protein.

According to a third aspect of the present invention the present invention provides a heat shock protein linked to one or more immunogenic peptides of CCR5 or one or more immunogencially similar peptides.

The term "immunogenically similar peptides" refers to peptides which gives rise to a substantially identical immunogenic response to that generated by a immunogenic peptide of CCR5. An immunogenic response can be determined to be substantially identical if substantially the same degree of immunological protection is obtained, e.g. by measuring antibody responses and/or T-cell proliferative responses. Methods for determining whether immunological protection has been obtained are described in Lehner et al., Nature Medicine, 2, 767–775, 1996.

Preferably the one or more immunogenic peptides of CCR5 comprise the sequence MDYQVSSPIYDINYYTSEPC (SEQ ID No:1); HYAAAQWDFGNTMCQ (SEQ ID No:2); CSSHFPYSQYQFWKNFQTLK (SEQ ID No:3); DINYYTSEPCQKINVKQIAAR (SEQ ID No:4), RSQKEGLHYTCSSHFPYSQY (SEQ ID No:5) or NTFQ-EFFGLNNCSSSNRLDQ (SEQ ID No:6).

The immunogenic peptides of CCR5 can be covalently linked or non-covalently linked to the heat shock protein as described above in respect of the first aspect of the present invention.

The third aspect of the present invention also provides a pharmaceutical composition comprising the heat shock protein according to the third aspect of the present invention in combination with a pharmaceutically acceptable excipient, carrier, adjuvant or vehicle.

The third aspect of the present invention also provides the heat shock protein according to the third aspect of the present invention for use in therapy.

The third aspect of the present invention also provides the use of a heat shock protein according to the third aspect of the present invention in the manufacture of a medicament for the treatment or prophylaxis of an infectious disease.

The third aspect of the present invention also provides a method of treatment or prophylaxis of an infectious disease, comprising administering to a patient in need of such treatment or prophylaxis an effective dose of a heat shock protein linked to one or more immunogenic peptides of CCR5 or one or more immunogenically similar peptides.

According to a fourth aspect of the present invention the present invention provides a peptide from an extracellular domain of CCR5 or an immunogenically similar peptide, for use as an immunogenic peptide.

Preferably the peptide from an extracellular domain of CCR5 comprises the sequence MDYQVSSPIYDINYYTSEPC (SEQ ID No: 1); HYAAAQWDFGNTMCQ (SEQ ID No: 2); CSSHFPYSQYQFWKNFQTLK (SEQ ID No: 3), DINYYTSEPCQKINVKQIAAR (SEQ ID No: 4), RSQKEGLHYTCSSHFPYSQY (SEQ ID No: 5) or NTFQ-EFFGLNNCSSSNRLDQ (SEQ ID No: 6). It is further preferred that the peptides from an extracellular domain of CORS consist of the sequence MDYQVSSPIYDINYYTSEPC SEQ ID No:1; HYAAAQWDFGNTMCQ SEQ ID No:2); CSSHFPYSQYQFWKNFQTLK (SEQ ID No:3), DINYYTSEPCQKINVKQIAAR (SEQ ID No:4), RSQKEGLHYTCSSHFPYSQY (SEQ ID No:5) or NTFQ-EFFGLNNCSSSNRLDQ (SEQ ID No:6).

The fourth aspect of the present invention also provides a peptide from an extracellular domain of CCR5 for use in therapy.

The fourth aspect of the present invention also provides the use of one or more peptides from an extracellular domain of CCR5 to generate an antibody molecule having affinity for CCR5. The antibody molecule may be a polyclonal antibody, a monoclonal antibody or an antigen binding fragment thereof such as a Fab, F(ab')$_2$ or Fv fragment. Methods for generating such antibody molecules are well known to those skilled in the art.

The fourth aspect of the present invention also provides an antibody molecule having affinity for a peptide from an extracellular domain of CCR5. Preferably the antibody molecule has affinity for a peptide comprising the sequence MDYQVSSPIYDIDYYTSEPC (SEQ ID No: 7), MDYQVSSPIYDINYYTSEPC (SEQ ID No: 1); HYAAAQWDFGNTMCQ (SEQ ID No: 2); CSSHFPYSQYQFWKNFQTLK (SEQ ID No: 3), DINYYTSEPCQKINVKQIAAR (SEQ ID No: 4), RSQKEGLHYTCSSHFPYSY (SEQ ID No: 5) or NTFQEFFGLNNCSSSNRLDQ (SEQ ID No: 6).

The fourth aspect of the present invention also provides the use of one or more peptides from an extracellular domain of CCR5 or the antibody molecule according to the fourth aspect of the present invention in the manufacture of a composition for the treatment or prophylaxis of an SIV or HIV infection.

The present invention also provides a method of treatment or prophylaxis of an SIV or HIV infection comprising administering to a patient in need of such treatment or prophylaxis an effective dose of a peptide derived from an extracellular domain of CCR5 or an antibody molecule according to the fourth aspect of the present invention.

According to the first, second and third aspects of the present invention a heat shock protein is delivered to a cell in order to enhance the production of one or more chemokines by the cell. The cell may be present in vitro or in vivo. Preferably the cell is present in vivo and the heat shock protein, which may comprise a linked peptide, is delivered to the individual resulting in increased production of one or more chemokines. Increased production of chemokines results in an immune response which can prevent microbial and viral infections, and tumour development.

The present invention also provides a pharmaceutical composition comprising a heat shock protein linked to one or more immunogenic peptides of CCR5 or one or more immunogenically similar peptides in combination with a pharmaceutically acceptable excepient, carrier, adjuvant or vehicle.

The present invention also provides a pharmaceutical composition comprising a peptide from an extracellular domain of CCR5 or an immunogenically similar peptide, or an antibody molecule having affinity for a peptide from an extracellular domain of CCR5, in combination with a pharmaceutically acceptable excepient, carrier, adjuvant or vehicle.

The heat shock protein or immunogenic peptide of the present invention can be delivered to an individual in combination with any pharmaceutically acceptable carrier, adjuvant or vehicle. Pharmaceutically acceptable carriers, adjuvants and vehicles that may be used include, but are not limited to, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protomine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene—block polymers and wool fat.

The heat shock proteins or peptides of the present invention may be administered orally, parentally, by inhalation spray, topically, rectally, nasally, buccally, vaginally or by an implanted reservoir. Preferably, the heat shock proteins or peptides of the present invention are administered by injection. The term "parenteral" as used herein includes subcutaneous, intracutaneous, intravenous, intramuscular, intraarticular, intrasynovial, intrastemal, intrathecal, intralesional and intracranial injection or infusion techniques.

The heat shock protein or peptides may be delivered in the form of a sterile injectable preparation, for example as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parentally-acceptable diluent or solvent, for example as a solution in 1,3-butanediol. Among the acceptable vehicles and solvents that may be employed are mannitol, water, Ringer's solution and isotonic sodium chloride solution. In addition, sterile, fixed oils are conventially employed as a solvent or suspending medium. For this purpose, any bland fixed oil may be employed including synthetic mono- or di glycerides. Fatty acids such as oleic acid and its glyceride derivatives are useful in the preparation of injectables, as are naturally pharmaceutically acceptable oils such as olive oil or castor oil, especially in their polyoxyethyated versions. These oil solutions or suspensions may also contain a long chain alcohol diluent or dispersant such as Ph. Helv or a similar alcohol.

The heat shock proteins and peptides of the present invention may also be administered as a fluid or in the form of suppositories for rectal administration. The suppository can be prepared by mixing the heat shock proteins or peptides of the present invention with a suitable non-irritating excipient which is solid at room temperature but liquid at the rectal temperature and therefore will melt in the rectum to release the heat shock proteins or peptides. Such materials include but are not limited to cocoa butter, bee's wax and polyethylene glycols.

Topical administration of the heat shock proteins or peptides may be desirable when the desired treatment involves areas or organs readily accessible for topical application. For application topically to the skin, the heat shock protein should be formulated with carriers for topical administration, such as, but not limited to mineral oil, liquid petroleum, white petroleum, propylene glycol, polyoxyethylene, polyoxypropylene compounds, emulsifying wax and water. Alternatively, the heat shock proteins or peptides can be formulated with a suitable lotion or cream, or dissolved in a carrier. Suitable carriers include but are not limited to mineral oil, sorbitan monosterate, polysorbate 60, cetyl esters, wax, cetearyl alcohol, 2-octyldodecanol, benzyl alcohol and water. The heat shock proteins or peptides can be applied topically to the lower intestinal tract by a rectal suppository formulation or as a suitable enema formulation.

The heat shock proteins or peptides of the present invention may be administered by nasal aerosol or inhalation. Suitable compositions for such administration can be prepared according to techniques well known to those skilled in the art of pharmaceutical formulation and can be prepared as solutions in saline, employing benzyl alcohol or other preservatives, absorbtion promoters to enhance bio-availability, fluorocarbons, and/or other solublising other dispersing agents known in the art.

The following examples, with reference to the figures, are offered by way of illustration and are not intended to limit the invention in any manner.

The figures show:

FIG. 1 shows schematically the dual protection against protection HIV/SIV by the generation of β-chemokines, and antibodies to CCR5.

FIG. 2 shows the effect on HIV replication of adding increasing concentrations of (a) monoclonal antibody having affinity for CCR5 to 0.2 mg/ml of the β-chemokines (also referred to as 3 CC chemokines) and (b) the three CC chemokines to one 1 mg/ml of a monoclonal antibody to CCR5.

FIG. 3 shows serum Ig antibodies before and after the third immunisation of a macaque with HSP70 (group I), HSP70 with SIVp27 and gp120 (group II) and HSP70 with the three defined CCR5 peptides (group III).

FIG. 4 shows T cell proliferation before and after the third immunisation of a macaque with HSP70 (group I), HSP70 with SIVp27 and gp120 (group II) and HSP70 with the three defined CCR5 peptides (group III).

FIG. 5 shows serum IgG and IgA antibodies to CCR5 or its extracellular peptides, after immunisation (×3) with CCR5 or the three specifically defined CCR5 peptides.

FIG. 6 shows T cell proliferation stimulated by CCR5 or the three specific CCR5 peptides, after immunisation (×3).

FIG. 7 shows the T and B cell epitope mapping of the extracelluar domains of CCR5 after immunisation with CCR5.

FIG. 8 shows the binding of $^{125}$I-labelled CCR5 loop 2 peptide (89–102) to *M. tuberculosis* HSP70.

FIG. 9 shows T cell proliferative responses to CCR5 and its extracellular domains in PBMC, spleen and lymph nodes after immunisation of 4 macaques each with CCR5 or one of the 3 CCR5 peptides.

FIG. 10 shows the concentration of 4 β-chemokines after immunisation with N-terminal (aa1–20), 1st loop (aa89–102) and 2nd loop (aa178–197) peptides or CCR5 lysate in alum in 4 representative macaques.

EXAMPLES

Materials and Methods

Preparation of HSP70 and HSP65

*M. tuberculosis* HSP70 was prepared in *E. coli* as described in Mehlert et al., Mol. Microbiol., 3, 125–130, 1989. HSP65 was obtained from StressGen, Inc.

Preparation of SIV Antigens

Recombinant SIV mac 251 gp120 was expressed in Baculovirus infected cells (Simmons et al., Science, 276, 276–279, 1997) and recombinant SIV p27 was generated in pGEX-3×as a glutathione s-transferase fusion protein. Both preparations were either covalently linked to HSP70 by 0.0025% glutaraldehyde (Sigma Fine Chemicals Ltd.) or mixed in equal concentrations as described below.

Preparations of CCR5 and the Peptide Constituting the 4 Extracellular Domains Baculovirus (*Autographa Californica* nuclear polyhedrosis virus) was used to express the protein in the insect cell line *Spodoptera Frugiperda* 9 (SF9). Briefly, high titre (10 PFU/ml) baculovirus expressing CCR5 was used to infect SF9 cells at a multiplicity of infection of 10 for 72 hours. The recombinant baculovirus expressing CCR5 was prepared using the full length gene of human CCR5 (Rucker et al., Cell, 87, 437–446, 1996), PCR cloned into the baculovirus transfer vector pAcC129.1. A 6 His affinity tag was added to the 3' end of the gene via the reverse oligonucleotide used in the PCR reaction. This DNA construct was then used to generate a baculovirus expressing CCR5+6 His as described earlier for SIV gp120 (Doyle et al., J. Immunol. 69, 1256–1260, 1995). Expression of the gene was confirmed by PCR on infected cells. A cell lysate was prepared by lysing the cells in PBS+1% N-octylglucoside and removing insoluble material by centrifugation. A control SF9 lysate was also used.

The 6 peptides and a random unrelated 20$^{er}$ was purchased from Neosystem Laboratories (Strasbourg, France) and the sequences of the 20$^{ers}$ are shown below.

N-terminal (aa 1–20): Met-Asp-Tyr-Gln-VaI-Ser-Ser-P ro-I Le-Tyr Asp-ILe-Asn-Tyr-Tyr-Thr-Ser-Glu-Pro-Cys (SEQ ID No: 1) N-terminal (aa11–31): Asp-ILe-Asn-Tyr-Tyr-Thr-Ser-Glu-Pro-Cys-Gln-Lys-ILe-Asn-VaI-Lys-Gln-ILe-Ala-Ala-Arg (SEQ ID No: 4) (macaque differs from the human sequence in Thr-9 (lie) and Asp 13 (Asn) 1St loop (aa 89–102): His-Tyr-Ala-Ala-Ala-Gln-Trp-Asp-Phe-GIy-Asn-Thr-Met-Cys-Gln (SEQ ID No:2) 2nd loop (168–187): Arg-Ser-Gln-Lys-Glu-GIy-Leu-His-Tyr-Thr-Cys-Ser-Ser-His-Phe-Pro-Tyr-Ser-Gln-Tyr (SEQ ID No: 5) (macaque differs from the human sequence in Lys 171 (Arg)) 2nd loop (aa178–197): Cys-Ser-Ser-His-Phe-Pro-Tyr-Ser-Gln-Tyr-Gln-Phe-Trp-Lys Asn-Phe-Gln-Thr-Leu-Lys (SEQ ID No: 3) 3rd loop (aa258–279): Asn-Thr-Phe-Gln-Glu-Phe-Phe-GIy-Leu-Asn-Asn-Cys-Se Ser-Ser-Asn-Arg-Leu-Asp-Gln (SEQ ID No: 6)

Immunisation Schedule

Schedule A

Four groups of a total of 12 rhesus macaques were immunised 3 times at about monthly intervals and 2 control macaques were not immunised. Three macaques were immunised with 200 mg of the CCR5 preparation in alum (AluGel, Uniscience, London, UK) by the IM route. A group of 4 macaques was given 200 mg of the CCR5-derived N-terminal peptide in Alum; 3 macaques received p1–20 and 1 p11–31 in Alum in targeting SC inguinal lymph nodes (TLN), as described previously (Lehner et al., J. Immunol., 153, 1858–1868, 1994). The remaining 5 macaques were immunised by the TLN route, using synthetic peptides from the sequence of the 1st loop (aa 89–102) (n=3) or 2nd loop (aa 178–197) (n=2) (see above). Detailed autopsy examinations were carried out in 4 macaques with removal of lymphoid tissues, about 2 months after the last immunisation.

Schedule B

Four groups of a total of 18 macaques were studied, of which 5 were non-immunised controls and all but I were immunised by the IM route. Group I (n—5) was injected 100 μg of HSP70 IM into the arm (deltoid muscle) and 100 μg into the leg (gluteal muscle) ×3 at 6 and 8 week intervals. Group 2 macaques (n=4) were immunised similarly, except that the vaccine consisted of 200 μg of HSP70 glutaraldehyde linked to 200 mg of SIV gp120 and 200 mg SIV p27 (obtained from Autogen Bioclear Ltd.). Group 3 animals (n=4) were immunised IM as the other two groups, except that 3 of the 4 macaques were given in addition to HSP70, SIV gp120 and p27 the 3 CCR5 peptides (N terminal p1–20, 1st loop (p89–102) and 2nd loop p178–197), one half of which was mixed and the other half covalently linked to HSP70 covalently linked to 100 μg of each of the 3 peptides and the vaccine was administered by the TLN route 3×at about monthly intervals and boosted IM 4 months later.

Serum IgG and IgA Antibodies

Specific serum antibodies to CCR5 and its extracellular peptides were assayed by ELISA as described previously (Lehner et al., PNAS USA, 90, 8638–8642, 1993). Briefly plates were coated with a predetermined optimal concentration of antigen (1 mg/ml) and with a random 20-base peptide (R20) as a control antigen and incubated with doubling dilutions of test samples. Bound antibody was detected by incubation with rabbit IgG anti-monkey IgA (8 mg/ml) (Nordic Immunological Laboratories, Tilburg, The Netherlands) or IgG (2 mg/ml; Sigma), followed by affinity-purifie d goat anti-rabbit IgG-alkaline phosphatase conjugate (Sigma). The IgG and IgA antibody titres are presented as reciprocals before and after each immunisation.

T Cell Proliferative Responses to CCR5 and the Peptides

T cell cultures were set up by separating mononuclear cells from defibrinated blood by Lymphoprep (NYCOMED, Oslo) density gradient centrifugation before and after immunisation from all macaques (Lehner et al., J. Immunol., 1,1858–1868, 1994). The cells were cultured without and with 1 and 10 mg/ml of CCR5 and its extracellular peptides, a control peptide (R20) or Coneanavalin A in 96-well round-bottomed plates (Costar, Cambridge, Mass.), containing RPMI 1640 (Gibco), as described before (Lehner et al., J. Immunol., 153, 1858–1868, 1994). The results were expressed as stimulation indices (SI, ratio counts with and without antigen), as well as counts per minute (cpm) before and after each immunisation for cultures stimulated with the optimum concentration of antigen. All cultures yielded high stimulation indices and counts with Concanavalin A, and no significant increase in counts was seen with the control peptide (data not presented).

T and B Cell Epitope Mapping

The T cell proliferative responses and IgG antibodies to the 6 overlapping peptides of the 4 extracellular domains of CCR5 were determined using PBMC and sera from the CCR5 immunised macaques. The methods are described above and the results are presented as SI and reciprocal IgG antibody titres to each peptide, and compared with the responses to the CCR5 construct.

Lymphoid Tissue Examination at Autopsy

Autopsies were carried out on 4 macaques in order to study the T cell proliferative responses to the CCR5 preparation and its extracellular domains in related and unrelated lymphoid tissues. After exsanguination, the spleen, internal and external iliac, superior and inferior mesenteric, bronchial, axillary and submaxillary lymph nodes were removed. The tissues were cut into fragments, teased apart, and passed through a fine mesh and processed. The cell suspensions were collected, washed with RPMI and then cultured with CCR5 and the peptides as described above.

Serum Inhibition of SIV Replication

To assay serum inhibition of SIV replication, PHA (phytohaemagglutinin) stimulated human CD4$^+$ T cells were infected with SIV J5 molecular clone in the presence of serum IgG antibodies (10 and 100 mg/ml) as described by Lehner et al., Eur. J. Immunol., 29: 2427–2435, 1999.

The cells were then plated on to 96 well plates ($2\times10^5$ cells/well) and cultured in 20% IL-2 medium (Lymphocult-T-LF, Biotest, Solihull, UK) containing the serum. The cultures were re-fed at day 2 and day 5 with the same medium, and by day 7 the supernatants of the cultures were removed to determine the RT activity by using the Quan-T-RT kits (Amersham, Buckinghamshire, UK).

SUV (or HIV) Suppressor Factor (SIV-SF) Assay

The preparation of CD8-SF was carried out according to the method previously described (Mackewicz et al., AIDS Res & Hium. Retroviruses, 8, 629–40, 1992; Lehner et al., Nature Med. 2, 767–775, 1996). Simian PBMC were prepared from defibrinated blood by gradient centrifugation on Lympho-Pre (NYCOMED, Oslo). Lymph nodes and spleen were collected 1 week after final immunization at autopsy. Splenic and lymph node mononuclear cells were obtained by cutting and teasing the lymphoid tissues. CD8$^+$ cell populations were enriched by panning, using negative selection. CD4$^+$ cells were removed with anti-CD4 Mab (OKT4 hybridoma culture supernatant), monocytes and B-cells with anti-immunoglobulin antibodies (Serotec, Oxford, UK). The cells were then stimulated for 3 days with 10 mg/ml PHA (Sigma) in 10% FCS-RPMI medium supplemented with 2 mM glutamine, 100 mg/ml of penicillin and streptomycin. CD8$^+$ blasts were washed and resuspended at $3\times10^6$/ml in the same medium containing 20% IL-2 (Biotest, Solihull, UK). After 2 days incubation at 37° C. in 5% CO$_2$, the culture supernatant was collected and the cells were replenished with fresh medium. This procedure was repeated up to 3 times. The collected supernatants were filtered through a 0.45 mm filter and stored at −70° C. for the CD8-SF activity assay.

CD8-SF Activity Assay

Enriched CD4$^+$ cells were prepared from simian PBMC by negative selection using Mab to CD8, as described above. The CD4$^+$ cells were stimulated for 3 days with 10 mg/ml of PHA in 10% FCS-RPMI medium. The cells were washed and then 106 CD4$^+$ cell pellets were incubated with 100 ml of SIVmac 251 stock preparation (containing 35000 cpm RT activity) for 2 h. After incubation, free virus was washed off with culture medium and $2\times10^5$ cells per well were plated onto 96-well tissue culture plates (Costar, Cambridge, Mass.). To assay the activity of CD8-SF, 100 ml of CD8$^+$ cell culture supernatant diluted at 1:2 and 1:5 was added at the start of the culture to SIV infected CD4$^+$ cells. As a control CD4$^+$ cells were cultured in medium alone. After incubation for 2 days, 100 ml per well of culture fluid was removed for monitoring RT activity and replaced with 100 ml per well of diluted CD8$^+$ cell supernatant (1:2 or 1:5) or control medium. This was repeated every 2 days for up to 14 days and the RT activity was determined by Quan-T-RT kits (Amersham, Buckinghamshire, UK).

β-Chemokine Assay for RANTES, MIP-1α and MIP-1β

The chemokines RANTES, MIP-1α, MIP-1β and MCP-1 were assayed in the culture supernatants generated for the CD8-SF, using the specific ELISA kits (R&D System, Oxon, UK). Optimum conditions were established with the CD8$^+$ cell culture supernatant diluted at 1:8. The results were corrected for the dilution factor and presented in pg/ml.

Non-Covalent Loading of HSP70 with Peptide

The three CCR5 peptides (N-terminal 1–20, 1$^{st}$ loop 89–102, 2$^{nd}$ loop 178–197) were dissolved at 1–2 mg/nl in phosphate buffered saline (PBS) supplemented with 3 mM MgCl$_2$ and 10 mM dithiothreitol (DTT) where cysteine was present in the peptide. HSP70 was dissolved also at 1–2 mg/ml in PBS supplemented with 3 mM MgCl$_2$. For loading with peptide, HSP70 was incubated with 10–20 fold molar excess of peptide (approximately 1:3.5–1:1.75 w/w ratio of HSP70:peptide) at 37° C. for 1–2 h. In some experiments, unbound peptide was removed by centrifugal dialysis using a centrifugal concentrator (10,000 M$_r$ cut-off, Flowgen). The retentate was washed three times with 2 ml PBS supplemented with DTT and MgCl$_2$ as above using the centrifugal concentrator and finally concentrated to the required concentration for subsequent use.

Glutaraldehyde Linkage of Peptides to HSP70

The CCR5 peptides (or SIV gp120 and p27 peptides) and HSP70 were dissolved (separately) at 1 mg/ml in sterile saline. Equal volumes of HSP70 and peptide were combined and glutaraldehyde was added to give a final concentration of 0.0025%. The mixtures were incubated for 2 h at room temperature and then dialysed against sterile saline overnight at 4° C. If necessary, HSP70-peptide complexes were concentrated by use of a centrifugal concentrator as described above.

Linkage of Peptides to HSP70 by Use of the Cross-Linker SPDP

The heterobifunctional cross-linking reagent N-succinimydyl-3(2-pyridyldithio) propionate (SPDP) (Sigma Pine Chemicals Ltd.) was used to couple HSP70 to peptides according to the manufacturer's instructions. HSP70 was dissolved in 0.1 M sodium phosphate pH 7.5 containing 0.1M NaCl. SPDP was dissolved in ethanol at a concentration of 20 mM and added to give a molar ratio of 20:1 of SPDP to HSP70. The reaction was allowed to proceed at room temperature for 30 min. Excess SPDP was removed by gel filtration on a Sephadex G25 column and buffer exchanged into 0.1M acetate buffer pH 4.0 containing 0.1M NaCl. The 2-pyridyl disulphide groups were reduced with 50 mM DTT for 20 min at room temperature. Excess reducing agent and pyridine 2-thione were removed by buffer exchange into 0.1M sodium phosphate pH 7.5 on a Sephadex G25 column. The thiolated HSP70 was mixed with CCR5 peptides (these did not require thiolation as all include a Cys residue) and incubated overnight at room temperature to form disulphide-linked conjugates.

Linkage of Peptides to CTB (Cholera Toxin B Subunit by Use of the Cross-Linker SPDP The same method as described above was used to link peptides to CTB. CTB was obtained from Sigma Chemical Co.

Techniques for Determining Whether Covalent Binding of Peptide to HSP70 Needs to be Carried Out.

a) Mass Spectrometry

HSP70 was loaded non-covalently with each of the CCR5 peptides as described above and unbound peptide was removed by washing in a centrifugal concentrator with PBS. Bound peptide was separated from HSP70 by reversed-phase HPLC (Brownlee Aquapore RPC81 mm×100 mm column) with 0.1% formic acid in acetonitrile (10–60% gradient) as fluid phase. To allow quantitation of peptide, IPLC was linked to mass spectrometry with electrospray ionisation on a Micromass UK Ltd. Platform 1 instrument. This assay determines quantitatively the amount of peptide associated with HSP70. Control samples include HSP70 with no added peptide and peptide incubated with no HSP70.

b) Immunisation with Peptide Bound Non-Covalently or Covalently Linked to HSP70

C57BL/6J mice were immunised intraperitoneally (×2) with CCR5 peptides either bound non-covalently to HSP70 or covalently linked to HSP70 by treatment with glutaraldehyde as described above. The second immunisation was 4–6 weeks after the first and sera were taken 2 weeks after the second immunisation. Serum antibody levels were determined by enzyme linked immunosorbent assay (ELISA). Peptides (dissolved in PBS at 10 mg/ml) or HSP70 (at 2 mg/ml in PBS) were adsorbed to the wells of microtitre plates by incubation at 4° C. overnight. Wells were then washed with PBS before addition of 1% bovine serum albumin (BSA) in PBS for 1 h at room temperature. Wells were washed ×3 with PBS containing 0.001% Tween 20 (PBST) and serial dilutions of serum in PBS were added. Incubation was for 2–3 h at room temperature or overnight at 4° C. Plates were washed ×3 with PBST and incubated with alkaline phosphatase conjugated anti-mouse Ig antibody for 2 h at room temperature before washing with PBST as before. Substrate, p-nitrophenyl phosphate, was then added and the plate was developed for 30–60 min before addition of 3M $H_2SO_4$. Absorbance at 405 nm was determined. Results are expressed as the highest dilution giving an absorbance value of $\geq 0.2$.

The results show that the $1^{st}$ loop (89–102) and $2^{nd}$ loop (178–197) peptides bind the HSP70 pocket non-covalently, whereas the N-terminal peptide (1–20) does not and needs to be covalently linked to HSP70 to be immunogenic (Table 10). It is important to appreciate that no additional adjuvant was used.

c) Gel Electrophoresis Assay

HSP70 was incubated with $^{125}$I-labelled peptides as described above in PBS, supplemented with $MgCl_2$ and DTT, in the presence of varying concentrations of unlabelled peptide (0–10 fold molar excess over unlabelled peptide). Samples were analysed by polyacrylamide gel electrophoresis in the presence of sodium dodecyl sulphate using gels of 10% acrylamide. Peptide remains bound to HSP70 under these conditions if sample is not heated prior to electrophoresis (Peng et al., J. Imm. Methods, 204: 13–21, 1997). Binding was evident when migration of labelled peptide (approx. $M_r$ 2,000) was coincident with HSP70 as shown in FIG. 8.

Assay of Cell Surface CCR5 by Flow Cytometry

Freshly isolated PBMC were incubated with monoclonal antibodies to CCR5 (2D7), (e.g. antibody 2D7 purchased from Becton Dickinson). The cells were incubated with fluorescein isothiocyanate (FITC)-labelled rabbit anti-mouse IgG (Dako, Glostrup, Denmark) or with the latter alone as a control, and flow cytometry was performed using a fluorescence-activated cell sorter (FACScan; Becton Dickinson, Franklin Lakes, N.J.) running LYSIS II software for both acquisition and analysis.

EXAMPLE 1

The effect of Subcutaneous or Intramuscular Immunisation with HSP65 or HSP70

HSP65 was prepared from Mycobacterium bovis as described above and administered in sterile saline SC (200 µg) at monthly intervals (×3) to rhesus macaques according to immunisation schedule A. HSP70 was prepared from *M. tuberculosis* by Dr. M. Singh (Braunschweig, Germany) and administered SC as with HSP65. Four β-chemokines (Rantes, MIP-1α, MIP-1β and MCP-1) and suppressor factor (SF) were examined by stimulating enriched $CD8^+$ T cells with PHA and assaying the culture supernatant, as described before (Lehner et al., 1996 Nature Medicine, 2, 767–775). The results suggest the HSP65 or HSP70 administered SC (×3) in the proximity of the iliac lymph nodes (or IM; macaque 19, Table 1) induces an increase in the concentration of RANTES (×4–10), MIP-1α (×3–14), MIP-1β (×4.8–11) but not MCP-1 (Table mean increases after the 3rd immunisation over the pre-immunisation concentrations were ×7.4, 5.6 and 7.0 for RANTES, MIP-1α and MIP-1β respectively.

EXAMPLE 2

The Effect of SC Immunisation with HSP65 or HSP70 Covalently Linked to Synthetic Peptides Macaques were immunised with HSP70 covalently linked with glutaraldehyde to three synthetic peptides (N-terminal (1–2-), 1st loop (89–102) and 2nd loop (178–197)) derived from the extracellular domains of CCR5 as described above. The immunisation procedure was as described in Schedule A above. Immunisation in this manner also yielded increases in the concentrations of RANTES, MIPα and MIP-1β. Furthermore, initial immunisation with synthetic peptides adsorbed to alum, followed by the same peptides being covalently linked to HSP65 or HSP70 resulted in increases in the concentration of each of the 3 β-chemokines over those reached after the peptide in alum immunisation.

The immunisation elicited an increase in RANTES (2.7–5.5×), MIP-1α (1.9–6.0×) and MIP-1β (1.3–6.0×) (Table 1 part 11). The somewhat lower effect of peptide-linked HSP as compared with HSP alone on the concentration of β-chemokines might be accounted for by the treatment with glutaraldehyde which may have altered the β-chemokine inducing determinants on HSP. MCP-1 remained largely unchanged after immunisation. Stimulation of β-chemokines showed no obvious difference between HSP70 and HSP65.

EXAMPLE 3

The Effect of Mucosal (Rectal) Application of HSP70 or HSP65 Covalently Linked to SIV Antigens HSP70 or HSP65 was covalently linked to SIVgp120 or p27 using glutaraldehyde as described above for the CCR5 peptides. Direct atraumatic mucosal application of the conjugates yielded increased concentrations of RANTES (×8), MIP-1α (×10.5) and MIP-1β (×9) but not MCP-1 (Table 1, part IV). This was surprisingly as effective as SC-TILN (subcutaneous targeted iliac lymph node) immunisation with HSP70 or HSP65 alone (Table 1).

The examples described above indicate that HSP65 or HSP70 administered by any of the routes of immunisation, with or without the peptides will up-regulate the 3 β-chemokines which are known to prevent HUV or SIV binding to CCR5 coreceptors and thereby prevent these cells from being infected (Lehner et al., Immunological Reviews, 170, 183–196, 1999).

EXAMPLE 4

The Effect of Immunisation with the HSP65 or HSP70 on the Level of CD8-SF (Supressor Factor)

In vitro inhibition of SIV replication was assayed in cells from some of the macaques by stimulating separated $CD8^+$ T cells with PHA and using the culture supernatant to inhibit SIV growth in $CD4^+$ T cells. Immunisation with HSP70 alone induced an increase in CD8-SF from less than 50% to greater than 50% inhibition (Table 2,I). Similar results were found with the 3 other groups of macaques, immunised by the TILN route with HSP70 covalently linked to CTB (cholera toxin B subunit) or the 3 peptides (N-terminal (1–20), 1st loop (89–102) and 2nd loop (178–197)) described in Example 2, or by the rectal mucosal route with HSP65 linked to SIV gp120 or p27 (Table 2) described in Example 3.

As for the β-chemokines, immunisation with HSP70 or HSP65 generates CD8-SF by $CD8^+$ T cells which significantly inhibit SIV replication.

EXAMPLE 5

The Effect of Immunisation with HSP65 or HSP70 on the Expression of CCR5 on the Cell Surface of Blood Mononuclear Cells There was no obvious difference between immunisation with HSP65 and HSP70, so the results were analysed jointly. Immunisation according to schedule A elicited down-regulation of both the proportion and cell surface expression of CCR5 from 35.8 (±3.3)% to 23.2 (±8.6)%, with a corresponding decrease in the median fluorescence intensity (MFI, Table 2, I). This was evident after the 1st immunisation but there was no further change after 2 subsequent immunisations. The peptide-linked HSP70 showed rather similar responses, except that some fluctuation in the percentage and MFI was evident after the 2nd immunisation (Table 3, I). Immunisation with the peptides in alum also induced a decrease in the expression of CCR5 and, except for some fluctuation, remained unchanged after testing with the same peptide linked to HSP70 (Table 3, III).

EXAMPLE 6

T Cell Proliferate Responses to HSP65 to HSP70

A progressive increase in the mean SI was found with each immunisation according to schedule A, from 1.5 (±0.32) to 8.6 (±2.2) after 1st, 9.0 (±2.3) after 2nd, and 11.6 (±0.76) after 3rd immunisation (Table 4). The results were similar when HSP70 was administered by the TILN route, either covalently linked to SIV gp120 or p27 or following immunisation of peptides given in alum. Only mucosal immunisation with HSP65 covalently linked to SIV gp120 or p27 elicited lower SI of 3.6 and 7.7 after the 3rd immunisations (Table 4). It is evident that the predominantly $CD4^+$ T cell proliferative responses are dissociated from the $CD8^+$ T cell generated β-chemokines and CD8-SF.

EXAMPLE 7

Protection Against Simian Immunodeficiency Virus (SIV) Infection in Rhesus Macaques Immunised with HSP70 or HSP70 Linked to Peptides In a pre-clinical model of HIV infection 4 mature rhesus macaques were immunised monthly (×4) with either HSP70 by the IM route or with HSP70 covalently linked to 3 synthetic peptides (N-terminal (1–20), 1st loop (89–102) and 2nd loop (178–197)) administered by the TILN route (Table 5) in accordance with schedule A. Two control macaques were not immunised. About a month after the last immunisation the macaques were challenged intravenously with 10 M1D50 of live SIV mac 8980 virus. Infection of the macaques was monitored by the plasma bDNA-PCR method and showed that the 2 control macaques were infected, with plasma RNA levels over the first 6 weeks ($5 \times 10^5$ SIVmac RNA equivalents per ml (Table 5)). In contrast the macaque immunised with HSP70 alone (No.19) was completely protected. Macaques immunised by the TILN route with HSP70 covalently linked to the N-terminal with or without the 1st and 2nd loop of CCR5 showed significant decrease in the plasmaSIVmac RNA levels in 2 of the 3 animals ($1.7 \times 10^3$ and $1.3 \times 10^4$) (Table 5). These results in non-human primates indicate that immunisation with HSP70 alone or when linked to one or more of the extracellular domains of the CCR5 coreceptor elicits either sterilising immunity or a significant decrease in SIV virus load. This result of vaccination against SUV in macaques, which is the best model of protection against HIV, is of considerable significance. HSP70 can be seen to be an important agent in vaccination against HIV, and in view of its ability to generate β-chemokines and CD8-SF it can also be used to vaccinate against malignant tumours and in immunodeficiency conditions.

As indicated above, the 70 kD heat shock protein (HSP70) has been found to up-regulate β-chemokines (RANTES, MIP-1α and MIP-1β), as well as suppressor factor (SF) that inhibits simian immunodeficiency virus (SIV) replication when administered to macaques. The SIV-SF can be accounted for by the 3 β-chemokines but there is evidence that SIV-SF may have additional and as yet unidentified factor(s). HSP70 was linked to peptides (each $20^{er}$ in size) derived from the sequences of the extracellular domains of CCR5, to explore the potential of a dual mechanism of immunity against CCR5 in non-human primates, through antibodies blocking and β-chemokines down-regulating the co-receptor (FIG. 1). Antibodies to the 3 extracellular domains of CCR5 (N terminal, $1^{st}$ and $2^{nd}$ loop) were found in the HSP70-CCR5 immunized but not in the HSP70 immunized macaques (Table 8). However, both HSP70 and HSP70 linked to CCR5 immunized macaques showed similar increases in the 3 β-chemokines (Table 8).

The possibility that CC chemokines can enhance CCR5 antibody inhibition or conversely CCR5 antibodies can enhance CC chemokine inhibition of HIV replication was investigated. Indeed, a dose-dependent inhibition of HIV replication resulted from increased concentration of CC chemokines added to a sub-optimal inhibitory dose of CCR5 antibody and vice versa (FIG. 2). A mouse serum isotype control or a CC chemokine control (MCP-1) had no effect on HIV replication. This suggests that HIV inhibition with low concentrations of the 3 β-chemokines can be enhanced with antibodies to CCR5 and conversely low titres of antibodies can be enhanced by the 3 β-chemokines. The double binding of CCR5 by means of the β-chemokines and antibodies to CCR5 can be more effective in blocking and down-modulating CCR5 than the β-chemokines alone (FIG. 1).

Additional Evidence Demonstrating Protection from Challenge with SUV Infection in Macaques Immunized with HSP70 and the 3 CCR5 peptides, with or without SIVgp120 and p27

Additional evidence of a protective effect of immunization with HSP70, with the 3 CCR5 peptides (N-terminal (1–20), 1st loop (89–102) and 2nd loop (178–197)) and with or without SIV antigens was studied in 9 macaques; 4 immunized and 5 non-immunised controls. The macaques were challenged IV with 30 MID50 of SIVmac 8980. All 5 non-immunised macaques were infected, with a set point of plasma SIVmac RNA at 12 weeks of $3\times10^4$ to $3\times10^6$ copies per ml (Table 9). However, immunization with HSP70 and the 3 immunogenic extracellular domains of CCR5 (N terminal, aa 1–20, $1^{st}$ loop, aa 89–102 and $2^{nd}$ loop, aa 178–197) with or without the SIV antigens showed that 2 of the 4 macaques were either completely protected (No. 1) or showed a decrease in SIV plasma load below the set point ($10^4$ SIV copies per ml) (No. 2). Thus, CCR5 receptor directed antibodies and β-chemokines can elicit in vivo protection from SIV infection.

EXAMPLE 8

Immunogencity of the Extracellular Domains of the CCR5 Chemokine Receptor

The β-chemokine receptor CCR5 serves an important function in chemotaxis of lymphocytes, monocytes and dendritic cells. CCR5 is also the major co-receptor in most M-tropic HIV-1 infections. A baculovirus-generated CCR5 construct and peptides derived from the sequences of the 4 extracellular domains of CCR5 have been prepared as indicated above in order to study their immunogenicity in rhesus macaques.

Human CCR5 which shows 97% identity with rhesus macaque CCR5 and has been expressed in Baculovirus. Serum antibodies were readily elicited in macaques to the CCR5 administered with alum by the IM route. Both IgG and IgA antibodies to CCR5 were found in the 3 macaques by ELISA, with titres of up to 1:6400 (FIG. 5). In view of the poor immunogenicity of synthetic peptides and the weak adjuvanticity of alum, peptides derived from the extracellular domains of CCR5 were administered by the subcutaneous route in the proximity of the inguinal and external iliac lymph nodes which enhances the immune responses but avoids deep injection targeting the internal iliac lymph node. Indeed, raised serum IgG and IgA antibodies up to a titre of 1:3200 were elicited by the immunising N terminal peptide 1–20 (but not with peptide 11–31) and the 1st (89–102) and 2nd loop (178–197) but not the 3rd loop peptides (FIG. 5). The N-terminal peptide 1–20 failed to elicit antibodies in 1 of the 3 macaques, although the peptide induced a T cell proliferative response in that animal. Antibodies induced by immunisation with the 3 peptides failed to recognise the CCR5 preparation and this may be either due to the lack of correct conformational structure of the synthetic peptides or because the CCR5 construct had the human sequence, whereas the synthetic peptides had the rhesus macaque sequence. The latter interpretation would not apply to the 1st loop which shares the same amino acid sequence between human and rhesus macaque CCR5, and yet was immunogenic and was recognised by antibodies and T cells derived from the CCR5 construct immunised macaques (FIG. 6). Rectal washings were tested for antibodies to CCR5 but these were not detected in any one of the immunised macaques.

T Cell Proliferative Responses

As with antibodies, strong T cell proliferative responses were elicited with the CCR5 baculovirus in alum after 2 or 3 immunisations, with SI, mean (+sem) of 13.6 (+4.8) (FIG. 6). The 2nd loop peptide (178–197) elicited T cell proliferative responses after the 3rd immunisation, with SI of 13.5 which was comparable with that induced by the CCR5 preparation (FIG. 6). The N terminal peptide (1–20) yielded moderate SI (4.4±0.5), but peptide 11–31 failed to stimulate T cell proliferative or antibody responses. However, the 1st loop peptides failed to elicit T cell proliferation, unless the macaques were boosted with peptides covalently linked to HSP70 (SI 4.3±0.8, FIG. 6). T cell proliferative responses were not elicited to the CCR5 preparation by PBMC from any of the synthetic peptide immunised macaques.

T and B Cell Epitope Mapping

The 4 extracellular domains, with the 6 overlapping synthetic peptides were examined for T cell proliferation and B cell antibody binding after immunisation with the Baculovirus CCR5 preparation (FIG. 7). T and B cell epitopes were identified in the N terminal peptide 1–20, but not 11–31, although the latter overlaps by 10 residues with peptide 1–20. Only weak T and especially B cell epitopes were detected with the 1st loop peptide (p89–102). The 2nd loop peptide 178–197 however, expressed strong T and B cell epitopes and this was also found with the overlapping peptide 168–187 but only for the B cell epitope (FIG. 7). Surprisingly, neither T nor B cell epitopes were recognised by the 3rd loop peptide 258–279. The identification of these epitopes is largely consistent with the immunogenicity of the extracellular domains of CCR5 as demonstrated with the synthetic peptides (FIGS. 5 and 6).

Examination of Lymphoid Tissues for T Cell Proliferative Responses

In order to increase T cell responses to the peptide immunised macaques, they were boosted by the TILN route, twice at monthly intervals with the peptide covalently linked to HSP70 or 65, before the animals were killed. Autopsies were carried out on representative macaques from each of the 4 groups, removing most of the related and unrelated lymphoid tissues. The eluted mononuclear cells from these tissues were stimulated with each of the 6 peptides form CCR5, the Baculovirus grown CCR5 lysate, control Baculovirus lysate, concanvalin A or without any antigen. The results in each of the 4 groups showed largely specific T cell proliferative responses only to the immuunising CCR5 or its peptides by PBMC, splenic, internal iliac and inferior mesenteric lymph node cells (FIG. 8). No or minimal responses were induced by the superior mesenteric or auxillary lymph node cells, or by the bronchial, submandibular, or the tonsillar cells (not presented). The lymphoid tissue results were similar to those obtained by stimulation with SIV p27 particulate antigen after TILN immunisation (Lehner et al., J. Immunol., 153, 1858–1868, 1994). Immunisation with CCR5 elicited T cell proliferative responses with CCR5 lysate, as well as some or all of the peptides from the extracellular domains of CCR5 (except the 3rd loop) by PBMC, iliac and inferior mesenteric, but the splenic cells responded only to the CCR5 lysate. In contrast, the N terminal, 1st and 2nd loop peptides elicited specific T cells proliferation only to the immunising peptides of which the 2nd loop peptide appeared to be the most immunogenic but the T cells failed to respond to the CCR5 lysate. Cells from all the tissues responded normally to mitogenic stimulation with Con A (positive control) and failed to respond to the control Baculovirus lysate (data not presented).

Inhibition of SIV Replication by Serum Antibodies to CCR5

$CD4^+$ T cells infected with SIV were treated with sera from macaques immunised with CCR5 or the extracellular domains of CCR5. These sera at dilutions of 1:10 and 1:100 increased in the inhibition of SIV replication after immunisation with the CCR5 preparation (in ⅔ macaques), the N terminal peptide 1–20 (all 3 macaques), the 1st loop (all 3 macaques) and the 2nd loop peptides (in ½ macaques); N terminal peptide 11–30 failed to have any effect (Table 6). This functional assay is consistent with the concept that serum antibodies to CCR5 inhibit SIV replication by blocking access of SIV to the CCR5 co-receptor.

Inhibition of HIV Replication by the Combined Effect of Antibodies to CCR5 and β-Chemokines Dose-dependent inhibition of HIV replication by the 3 β-chemokines has been demonstrated in vitro (Cocci et al., Nature Med., 2, 1244–1247, 1996; Wang et al., PNAS USA, 95, 5223–5228, 1998). Mab to CCR5 also inhibited HIV replication, as was demonstrated previously (Lehner et al., Eur. J. Immunol. 29, 2427–2435, 1999) and with sera from macaques immunised with CCR5 or its extracellular domains (Table 6). The possibility that β-chemokines can enhance CCR5 antibody inhibition or conversely CCR5 antibodies can enhance β-chemokines replication resulted from increased concentration of β-chemolines added to a sub-optimal inhibitory dose of CCR5 antibody and vice versa was examined. This suggests that HIV inhibition with low concentrations of 3 β-chemokines can be enhanced with antibodies to CCR5 and conversely low titres of antibodies can be enhanced by 3 β-chemokines.

Generation of β-Chemokines

Immunisation with the CCR5 preparation induced increased concentrations of RANTES, MIP-1α and MIP-1β, but not MCP-1 (FIG. 9). Immunisation with the extracellular peptides of CCR5 also upregulated the concentrations of RANTES, MIP-1α and MIP-1β, with the exception of MIP-1β by immunisation of the 1st loop. However, the kinetics differed, especially with the N terminal peptide 1–20 and the 1st loop. The CCR5 construct and 2nd loop peptide (178–197) elicited the most consistent increase in the concentrations of the 3 β-chemokines, and it is noteworthy that these also induced the highest T cell proliferative responses (FIG. 6).

Cell Surface Expression of CCR5

Upregulation of the β-chemokines in vitro or in vivo downmodulates the cell surface expression of CCR5. By flow cytometry the effect of immunisation of CCR5 or its extracellular peptides on the cell surface expression (MFI) or proportion of $CCR5^+$ cells have been studied (Table 7). Immunisation with the CCR5 preparation induced no consistent effect on the MFI or proportion of CCR5. However, immunisation with the N terminal, 1st and 2nd loop peptides elicited a decrease in the MFI in all 6 macaques, from a mean (±sem) of 278.7 (±41.7) to 74.3 (±21.1) (Table 7). The proportion of cells expressing CCR5 was also decreased, though to a lesser extent in ⅚ macaques from 25.9 (±1.9)% to 18.6 (±3.3)%. The presence of β-chemokines that bind CCR5 and antibodies to CCR5 is a dual mechanism that downmodulates cell surface CCR5.

Immunisation with the Baculovirus generated CCR5 in alum induced CCR5-specific IgG and IgA and $CD4^+$ T cell proliferative responses. Furthermore, immunisation with CCR5 elicited significant T cell proliferation to the 1st (aa 89–102) and 2nd loop peptides (aa 178–197). T and B cell epitope mapping of the extracellular domains of CCR5 showed an immunodominant epitope within the 2nd loop (peptide 178–197) and immunodominant B cell and minor T cell epitope within the N terminal peptide (1–20), minor T and B cell epitopes within the 1st loop but the 3rd loop of CCR5 failed to elicit an immune response.

In addition to the ELISA a functional assay was used to study serum antibodies to CCR5. An increase in inhibition of SIV replication was demonstrable with serum antibodies (at 1:100 dilution) to the N terminal peptide (aa 1–20) from 8.1±3.4% before to 49.2±8.0% (mean±sem) after immunisation and 1st loop from 16.9±6.9% before to 38.0±11.6% after immunisation, but to a limited extent to the 2nd loop peptide (from 23.3 to 30.5%).

Examination of T cell proliferative responses to the extracellular domains of CCR5 in the lymphoid tissues showed that the specificity of the 3 immunising peptides stimulating PBMC was largely maintained in the iliac and inferior mesenteric lymph nodes, and the spleen. In contrast, immunisation with the whole CCR5 preparation elicited T cell responses to the 1st and 2nd loop and to a lesser extent the N-terminal (aa 1–20) in the iliac and inferior mesenteric lymph nodes and PBMC. Cells from the unrelated superior mesenteric, auxiliary, submandibular and bronchial lymph nodes failed to respond to any of the peptides or CCR5.

Investigation of β-chemokine concentrations revealed that immunisation with the CCR5 preparation and peptides derived from the sequences of the extracellular domains of CCR5 upregulated the concentrations of CD8-cell derived RANTES, MIP-1α and MIP-1β. Upregulation of the β-chemokines was found with each immunisation of the CCR5 preparation and the 2nd loop; however, this was delayed with the 1st loop and the N terminal peptide of CCR5 up to the 3rd immunisation for MIP-1α and MIP-1β. The kinetics of generation of the β-chemokines after immunisation with whole CCR5 and the 2nd loop were similar to those of T cell proliferative responses and to a lesser extent the IgA and IgG antibodies.

There is evidence both in vitro and in vivo that raised concentrations of β-chemokines downmodulates the cell-surface expression of CCR5. Here it is shown that antibodies to CCR5 may have a similar effect to β-chemokines in downmodulating CCR5 receptors. In the present example both anti-CCR5 antibodies and β-chemokines bind to CCR5. However, it was surprising to find that immunisation with the whole CCR5 construct largely failed to downmodulate CCR5. In contrast, the 2nd loop of CCR5 elicited the greatest inhibition in the cell surface expression of CCR5 (5–15 fold), and demonstrated high concentration of β-chemokines, antibodies to the 2nd loop of CCR5 and specific T cell proliferative responses. Indeed, the 2nd loop of CCR5 is functionally endowed with co-receptor function, ligand specificity, binding of M-tropic HIV and SIV, as well as T-tropic SIV and having the 32 base pair deletion. These findings indicate that T cell responses generated by immunisation with the 2nd loop of CCR5 can be of special significance in immunomodulation of inflammatory processes, autoimmunity and prevention of HIV transmission.

The inhibitory effect on HIV replication caused by a suboptimal concentration of RANTES, MIP-1α and MIP-1β was enhanced in a dose-dependent manner with Mab to both the 2nd loop and N terminal of CCR5. Conversely, the effect of suboptimal titre of these antibodies on HIV inhibition was enhanced by the 3 β-chemokines. Thus, a dual mechanism of blocking and possibly downmodulating CCR5 may operate, in which the 3 β-chemokines and antibodies to CCR5 may bind different or the same extracellular domains of CCR5 and thereby block the function of the receptor, as well as prevent HIV or SIV transmission.

It is shown that immunisation with CCR5 or its extracellular peptides (especially the 2nd loop), stimulates CD4$^+$ and CD8$^+$ T cells to elicit immune responses that result in specific anti-CCR5 antibodies, CD4 cell proliferation and CD8 cell generation of β-chemokines. Such stimulation has significant general effects on chemotaxis of naive and memory T cells, immature dendritic cells, macrophages and B cells, as well as specific effects on preventing or treating HIV or SIV infection.

Various publications are cited herein, the disclosures of which are incorporated by reference in their entireties.

The present invention is not limited in scope by the specfic examples and embodiments described herein. Various modifications of the present invention will be apparent to those skilled in the art from the description above and such modifications are intended to fall within the appended claims.

TABLE 1

The effect of immunisation with mycobacterial 65 or 70 kD HSP in rhesus macaques on the concentrations of β-chemokines (pg/ml) in experiments I, II and III SC targeted iliac lymph nodes (except No. 19 IM), and in IV rectal mucosal immunisations were carried out.

| | | RANTES | | | MIP-1α | | |
|---|---|---|---|---|---|---|---|
| No. | HSP | Pre-Im 0 | 2 | Post-Im 3 | Pre-Im 0 | 2 | Post-Im 3 |
| I HSP | | | | | | | |
| 21 | HSP65 | 80 | 88 | 808 | 1256 | 3592 | 3808 |
| 89 | HSP65 | 176 | 384 | 1128 | 352 | 1336 | 4816 |
| 92 | HSP70 | 293 | 1248 | 1328 | 910 | 4240 | 4624 |
| 19 | HSP70* | 571 | ND | 4987 | 538 | ND | 4010 |
| Mean (n = 4) | | 280 | 573 | 2063 | 764 | 3056 | 4314 |
| (±sem) | | 106 | 348 | 981 | 201 | 880 | 241 |

| | | MIP-1β | | | MCP-1 | | |
|---|---|---|---|---|---|---|---|
| No. | HSP | Pre-Im 0 | 2 | Post-Im 3 | Pre-Im 0 | 2 | Post-Im 3 |
| I HSP | | | | | | | |
| 21 | HSP65 | 136 | 1520 | 1488 | 4456 | 4144 | 3232 |
| 89 | HSP65 | 224 | 584 | 1656 | 6384 | 7544 | 6624 |
| 92 | HSP70 | 619 | 1272 | 5440 | 7936 | 8208 | 6432 |
| 19 | HSP70* | 755 | ND | 3658 | 3281 | ND | 4374 |
| Mean (n = 4) | | 434 | 1125 | 3060 | 5514 | 6632 | 5166 |
| (±sem) | | 150 | 280 | 934 | 1030 | 1259 | 821 |

| | | RANTES | | MIP-1α | | MIP-1β | | MCP-1 | |
|---|---|---|---|---|---|---|---|---|---|
| | | 0 | 4 | 0 | 4 | 0 | 4 | 0 | 4 |
| II Peptides linked to HSP | | | | | | | | | |
| 31 | HSP70 | ND | 1706 | ND | 1198 | ND | 1738 | ND | 4453 |
| 75 | HSP70 | 671 | 3234 | 1454 | ND | 1840 | 2483 | 4574 | 3930 |

*Administered IM

| | | RANTES | | | MIP-1α | | |
|---|---|---|---|---|---|---|---|
| | | Pre-Im 0 | Post pept.* 2/3 | Post-pept HSP 1 | Pre-Im 0 | Post-pept* 2/3 | Post-pept HSP 1 |
| III Peptide-Alum followed by Peptide-HSP | | | | | | | |
| 62 | HSP65 | 18.2 | 1928 | 2160 | 960 | 4208 | 5960 |
| 48 | HSP65 | 1304 | 1320 | 2896 | 1456 | 2832 | 6368 |
| 87 | HSP70 | 833 | 1344 | 2048 | 1454 | 1432 | 4496 |
| 97 | HSP70 | 536 | 2160 | 1760 | 1448 | 1496 | 3912 |
| mean (n = 11) | | 714 | 1688 | 2216 | 1330 | 2492 | 5184 |
| sem± | | 238 | 211 | 242 | 123 | 657 | 584 |

| | | MIP-1β | | | MCP1 | | |
|---|---|---|---|---|---|---|---|
| | | Pre-Im 0 | Post pept.* 2/3 | Post-pept HSP 1 | Pre-Im 0 | Post-pept* 2/3 | Post-pept HSP 1 |
| III Peptide-Alum followed by Peptide-HSP | | | | | | | |
| 62 | HSP65 | 213 | 3232 | 2824 | 5336 | 5352 | 6112 |
| 48 | HSP65 | 3416 | 4040 | 5088 | 4888 | 4784 | 4768 |
| 87 | HSP70 | 1840 | 1848 | 4368 | 4574 | 4632 | 4888 |
| 97 | HSP70 | 1072 | 1208 | 1360 | 5568 | 5280 | 5640 |
| mean (n = 11) | | 1635 | 2582 | 3410 | 5091 | 5012 | 5352 |
| sem± | | 680 | 644 | 831 | 223 | 179 | 318 |

| | | RANTES | | MIP-1α | | MIP-1β | | MCP-1 | |
|---|---|---|---|---|---|---|---|---|---|
| | | Pre-Im | Post-Im | Pre-Im | Post-Im | Pre-Im | Post-Im | Pre-Im | Post-Im |
| | | 0 | 3 | 0 | 3 | 0 | 3 | 0 | 3 |
| IV HSP-SIV - Mucosal administration | | | | | | | | | |
| 88 | HSP65-gp120 | | | | | | | | |
| 27 | HSP65-27 | 656 | 5432 | 736 | 7760 | 624 | 5752 | 5296 | 4992 |

*Administered with Alum

TABLE 2

CD8 suppressor factors generated by HSP70 or HSP65 in 4 immunisation strategies; in experimental I, II, III SC targeted iliac lymph nodes (except in No. 19 given IM) and in IV rectal mucosal immunisations were carried out.

I HSP CD8-SF (%)

| No. | HSP | Pre-IM | Post-IM |
|---|---|---|---|
| 92 | HSP70 | 34.2 | 75 |
| 19 | HSP70 | 13.2 | 78.3 |

II Peptides linked to CTB

| | | Pre-IM | Post-IM |
|---|---|---|---|
| 31 | HSP70 | 0 | 79.5 |
| 75 | HSP70 | 21.8 | 59.1 |
| 890 | HSP70 | 22.4 | 88.3 |
| 889 | HSP70 | ND | |

III Peptides-Alum followed by peptides-HSP

| | | Pre-IM | Post-IM | Post-HSP |
|---|---|---|---|---|
| 62 | HSP65 | ND | 64.5 | 90.5 |
| 87 | HSP70 | 20.3 | ND | 64.1 |

IV HSP-SIV Mucosal administration

| | | Pre-IM | Post-IM |
|---|---|---|---|
| 88 | HSP-65-gp120 | ND | |
| 27 | HSP65-p27 | 35 | 91 |

TABLE 3

The effect of immunisation with HSP65 or HSP70 on the cell surface expression of CCR5 on PBMC; in experiments I, II, III SC targeted iliac lymph nodes (except no. 19, IM) and in II rectal mucosal immunisations were carried out.

| | | Pre-Im | | Post-1 | | Post-2 | | Post-3 | |
|---|---|---|---|---|---|---|---|---|---|
| No. | HSP | % | MFI | % | MFI | % | MFI | % | MFI |
| | | | | I HSP | | | | | |
| 89 | HSP65 | 29.3 | 195 | 18.1 | 19.3 | 12.6 | 138 | 16.3 | 244 |
| 92 | HSP70 | 40.0 | 328 | 40.0 | 328 | 28.4 | 217 | 28.8 | 193 |
| 19 | HSP70 | 38.2 | 97 | 11.6 | 44 | 35.5 | 209 | 25.5 | 27.6 |
| Mean | | 35.8 | 206.7 | 23.2 | 130.4 | 25.5 | 188.0 | 23.5 | 154.9 |
| ±sem | | 3.3 | 66.9 | 8.6 | 99.0 | 6.8 | 25.1 | 3.7 | 65.3 |
| | | | | II Peptides linked to HSP | | | | | |
| 31 Triple | HSP70 | 19.4 | 204 | 7.5 | 149 | 17.5 | 211 | 17.8 | 64 |
| 75 2nd Loop | HSP70 | 21 | 114 | 11.4 | 116 | 19.1 | 199 | 17.7 | 22 |
| 890 DR1 | HSP70 | 32.3 | 281 | 33.7 | 85 | 44.7 | 89 | 26.4 | 136 |
| Mean | | 24.2 | 199.7 | 17.5 | 116.7 | 27.1 | 166.3 | 20.6 | 74.0 |
| ±sem | | 4.1 | 48.2 | 8.2 | 18.5 | 8.8 | 38.8 | 2.9 | 33.3 |

| | | Pre- | Imm | Post - pept. | | Post - pept HSP | | X1 | X2 |
|---|---|---|---|---|---|---|---|---|---|
| | | | | III Peptides - Alum followed by peptides - HSP | | | | | |
| 62 N. term | HSP65 | 266 | 30.5 | 20.4 | 116 | 23.5 | 71 | 28.7 | 128 |
| 48 2nd loop | HSP65 | 31.7 | 270 | 14.6 | 42 | 28.3 | 31 | 14.9 | 170 |
| 87 N. term | HSP70 | 30.5 | 426 | 20.3 | 125 | 25.4 | 176 | 19.6 | 145 |
| 97 1st loop | HSP70 | 24 | 368 | 22.1 | 143 | 32.8 | 64 | 11.6 | 73 |
| Mean | | 28.2 | 273.6 | 19.4 | 106.5 | 27.5 | 85.5 | 18.7 | 129.0 |
| ±sem | | 1.8 | 87.2 | 1.6 | 22.2 | 2.0 | 31.4 | 3.7 | 20.6 |
| | | | | IV HSP-SIV Mucosal administration | | | | | |
| 88 HSP65 - gp120 | | 42.7 | 46 | 28.3 | 9.4 | ND | | | |
| 27 HSP-65 - p27 | | 41.9 | 114 | 47.1 | 196 | 37.5 | 310 | 40.8 | 49 |

TABLE 4

T cell proliferative responses to HSP65 or HSP70 in 4 immunisation strategies; in experiments I, II, III SC targeted iliac lymph nodes (except in No. 19, given IM) and in IV rectal mucosal immunisations were carried out.

|  |  | Pre-Im | | Post-Immunisation | | | | | |
|---|---|---|---|---|---|---|---|---|---|
|  |  |  |  | 1 | | 2 | | 3 | |
| No. | HSP | SI | cpm | SI | cpm | SI | cpm | SI | cpm |
| I HSP | | | | | | | | | |
| 21 | HSP65 | 1.1 | 59 | 7.8 | 514 | ND | | 13 | 688 |
| 89 | HSP65 | ND | | 2.7 | 350 | 4.8 | 624 | 10.1 | 808 |
| 92 | HSP70 | 2.1 | 245 | 10.7 | 1988 | 12.6 | 2151 | 12.9 | 2114 |
| 19 | HSP70 | 1.2 | 181 | 13.0 | 1070 | 9.7 | 640 | 10.6 | 879 |
| Mean | | 1.5 | | 8.6 | | 9.0 | | 11.6 | |
| ±sem | | 0.32 | | 2.2 | | 2.3 | | 0.76 | |

|  |  | Pre - Im | Post 1 | Post 2 | Post 3 |
|---|---|---|---|---|---|
| II Peptides linked to CTB | | | | | |
| 31 | HPS70-pept | | 89 | 5.9 | 436 | 6.5 | 488 | 13.3 | 1067 |
| 75 | HSP70-pept | 1.2 | 102 | 14.2 | 1241 | 12.1 | 1065 | 16.5 | 1711 |
| 890 | HSP70 pept | 0.9 | 87 | 1.0 | 136 | 6.7 | 603 | 6.8 | 722 |
| 889 | HSP70-pept | 1.2 | 123 | 4.8 | 470 | 5.9 | 560 | 8.8 | 792 |
| Mean | | 1.1 | | 6.5 | | 7.8 | | 11.3 | |
| ±sem | | 0.07 | | 2.8 | | 1.4 | | 2.2 | |

|  |  | Pre-Im | Post-pept X3 | Post-HSP X1 | X2 |
|---|---|---|---|---|---|
| III Peptide-Alum followed by peptides-HSP | | | | | |
| 62 | HSP65-pept | <2 | ND | ND | 9.8 833 |
| 48 | HSP65-pept | <2 | 1.3 127 | 5.8 684 | 12.8 1562 |
| 87 | HSP70 pept | <2 | 1.2 132 | 3.8 549 | 8.7 1131 |
| 97 | HSP70-pept | <2 | 1.3 124 | 13.6 1659 | 16.3 2037 |
| Mean SI | | <2 | 1.3 | 7.7 | 11.9 |
| ±sem | | | 0.03 | 2.9 | 1.7 |

IV HSP-SIV Mucosal administration

| 8 | HSP65gp120 | 1.5 | 160 | ND | | 1.2 | 127 | 3.6 | 367 |
| 9 | HSP65-p27 | 1.9 | 184 | ND | | 4.9 | 516 | 7.7 | 731 |
| Mean (=2) | | 1.7 | | | | 3.9 | | 5.6 | |

TABLE 5

Intravenous Challenge of HSP70 immunised macaques with 10 MID50 of live SIVmac 8980 virus

| Group | Immunisation | Pro-tection | CD8-SF % | 3 β-CC* pg/ml | SIV plasma load/ml** |
|---|---|---|---|---|---|
| 1 | Nil | 0/5 | 24.0 | 2455 | $10^5$–$10^7$ |
| 2 | HSP70 + peptides*** + SIVgp120 + p27 | 2/4 | | | |
| a) | HSP70 linked to CCR5 peptides*** | | 80 | 6262 | $2 \times 10^3$ |
| b) | HSP70 linked to CCR5 peptides*** + SVIGP120 + p27 | | | | Nil |
| c) | same as b) | | | | $1.3 \times 10^4$ |
| d) | same as b) | | | | $2 \times 10^6$ |

*RANTES, MIP-1α, MIP-1β
**6–8 weeks post-challenge
***N terminal (aa1–20), 1st loop (aa89–102), 2nd loop (aa178–197)

TABLE 6

In vitro serum inhibition of SIV replication before and after IM or
TILN immunisation with CCR5 or its extracellular peptides in Alum.
Inhibition of SIV replication in macaque CD4-enriched cells was determined
by the RT activity assay and expressed as % inhibition.

|  | Immunisation | | | Serum Inhibition (%) of SIV replication | | | |
|---|---|---|---|---|---|---|---|
|  |  |  |  | 1:10 | | 1:100 | |
|  | Antigen | Route | Macaque | Pre-Immunisation | Post-Immunisation | Pre-Immunisation | Post-Immunisation |
| 1 | CCR5 | IM | 23 | 7.8 | 29.4 | 0 | 16.9 |
| 2 | CCR5 | IM | 891 | 44.8 | 77.9 | 24.4 | 71.8 |
| 3 | CCR5 | IM | 56G | 57.2 | 38.8 | 22.7 | 29.2 |
|  | Mean (±sem) |  |  | 36.6 | 48.7 | 15.7 | 39.3 |
|  |  |  |  | (12.1) | (12.1) | (6.4) | (13.6) |
| 4 | N term 1–20 | TILN | 62 | 24.1 | 46.3 | 10.9 | 49.7 |
| 5 | N term 1–20 | TILN | 87 | 28.0 | 50.6 | 13.4 | 31.9 |
| 6 | N term 1–20 | TILN | 94 | 29.9 | 77.8 | 0 | 65.9 |
|  | Mean (±sem) |  |  | 27.3 | 58.2 | 8.1 | 49.2 |
|  |  |  |  | (1.4) | (8.0) | (3.4) | (8.0) |
| 7 | N term 11–30 | TILN | 64G | 27 | 20 | 8 | 16 |
| 8 | 1st loop 81–102 | TILN | 48 | 41.8 | 49.6 | 26.6 | 44.0 |
| 9 | 1st loop 81–102 | TILN | 97 | 14.9 | 56.5 | 0 | 10.9 |
| 10 | 1st loop 81–102 | TILN | 98 | 29.7 | 71.6 | 24.1 | 59.1 |
|  | Mean (±sem) |  |  | 28.2 | 59.2 | 16.9 | 38.0 |
|  |  |  |  | (6.4) | (5.3) | (6.9) | (11.6) |
| 11 | 2nd loop 178–197 | TILN | 6E | 47.2 | 45.4 | 38.4 | 38.4 |
| 12 | 2nd loop 178–197 | TILN | 75 | 34.1 | 45.3 | 8.2 | 22.6 |
|  | Mean |  |  | 40.6 | 45.4 | 23.3 | 30.5 |

TABLE 7

The effect of immunisation (x3) with baculovirus generated
CCR5 and its extracellular peptides from Alum on the cell surface
expression (median fluorescence intensity, MFI) and proportion
(%) of CCR5 assayed by flow cytometry in 9 macaques.

| Group | No. | CCR5 Domain | Route | MFI Pre–Post* | % Pre–Post* |
|---|---|---|---|---|---|
| I | 23 | CCR5 | IM | 93.1–214 | 24.3–17.3 |
|  | 891 | CCR5 | IM | 188–78 | 28.3–44.0 |
|  | 56G | CCR5 | IM | 245–281 | 23.4–21.2 |
| Mean |  |  |  | 175.4–191 | 25.3–27.5 |
| (±sem) |  |  |  | (36.2)–(48.8) | (12.3)–(6.8) |
| II | 62 | N terminal | TLN | 305–116 | 21.1–18.8 |
|  | 87 | (p1–20) | TLN | 426–125 | 30.5–20.3 |
| Mean |  |  |  | 336–120 | 25.8–19.6 |
| III | 48 | 1st loop | TLN | 240–135 | 23–8.8 |
|  | 97 | 1st loop | TLN | 368–33 | 26.6–34.3 |
| Mean |  |  |  | 306–139 | 24.8–21.5 |
| IV | 6E | 2nd loop | TLN | 219–14.4 | 33.3–11.4 |
|  | 75 | 2nd loop | TLN | 114–22.4 | 21–17.7 |
| Mean |  |  |  | 166–18.4 | 27.2–14.6 |
| Mean of 6 macaques immunised with the CCR5 peptides (±sem) |  |  |  | 278.7–74.3 (41.7) (21.1) | 25.9–18.6 (1.9) (3.3) |

TABLE 8

Antibody titres to CCR5 and β-chemokine concentrations in macaques immunised (x3) with HSP70 linked to CCR5 or HSP70 alone.

| Group | Immunisation N. terml. | Antibody Titres* 1st loop | 2nd loop | CCR5 | Chemokine concentration* RANTES | MIP-1α | MIP-1β |
|---|---|---|---|---|---|---|---|
| | | | I HSP70 + SIV + CCR5 | | | | |
| 5971 | 1:200 | 1:400 | 1:200 | 1:200 | 1902 | 3060 | 426 |
| 4592 | 1:200 | 1:400 | 1:200 | 1:100 | 200 | 3351 | 113 |
| 4841 | 1:200 | 1:200 | 1:200 | 1:100 | 952 | 846 | 610 |
| Mean (±sem) | 200(0) | 333(54) | 200(0) | 133(27) | 1018(402) | 2419(646) | 383(118) |
| | | | II HSP | | | | |
| 426 | 0 | 0 | 0 | 0 | 2005 | 1886 | 1018 |
| 491 | 0 | 0 | 0 | 0 | 866 | 1461 | 593 |
| 515 | 0 | 0 | 0 | 0 | 100 | 3000 | 1400 |
| 504 | 0 | 0 | 0 | 0 | 340 | 3611 | 337 |
| Mean (±sem) | | | | | 828(367) | 2490(429) | 837(203) |

*net increase from pre-immunisation level in titres or concentrations (pg/ml).

TABLE 9

Intravenous challenge of HSP70 immunised and control macaques with 10 MID50 of live SIVmac 8980 virus

| Group | Immunisation | No. of macaques | Pro- tection | SIV plasma load/ml* |
|---|---|---|---|---|
| 1 | Nil | 5 | 0/5 | $3 \times 10^4$–$3 \times 10^6$ |
| 2 | HSP70 ± CCR5 peptides** + SIV gp120 + 27 | 4 (1) (2) (3) (4) | 2/4 | Nil $10^{4***}$ $4 \times 10^5$ $10^7$ |

*12 weeks post-challenge
**N-terminal (aa1–20), 1st loop (aa89–102), 2nd loop (aa178–197)
***Decreased viral load

TABLE 10

Serum IgG antibody titres of BALBc mice immunised with CCR5-HSP70 complexes

| Immunogen | N terminal Loaded | Glut* | 1st loop Loaded | Glut | 2nd loop Loaded | Glut |
|---|---|---|---|---|---|---|
| N terminal | <50 | 200 | <50 | <50 | <50 | <50 |
| 1st loop | <50 | <50 | 800 | 50 | <50 | <50 |
| 2nd loop | <50 | <50 | <50 | <50 | 200 | <50 |
| HSP70 | 6400 | 6400 | 12800 | 12800 | 12800 | 3200 |

*glutaraldehyde linked

What is claimed is:

1. A chemokine or suppressor factor enhancer consisting of a heat shock protein capable of enhancing production of at least one chemokine and/or a suppressor factor by a cell in vivo, wherein at least one peptide is linked to said heat shock protein and at least one of said at least one peptide is derived from the extracellular domains of CCR5, and at least one of said at least one immunogenic peptide consisting of the sequence selected from the group consisting of MDYQVSSPIYDINYYTSEPC (SEQ ID No:1), HYAAAQWDFGNTMCQ (SEQ ID No:2), CSSHF-PYSQYQFWKNFQTLK (SEQ ID No:3), DINYYTSEPC-QKINVKQIAAR (SEQ ID No:4), RSQKEGLHYTCSSH-FPYSQY(SEQ ID No:5), and NTFQEFFGLNNCSSSNRLDQ (SEQ ID No: 6).

* * * * *

SEQUENCE LISTING

<160> NUMBER OF SEQ ID NOS: 7

<210> SEQ ID NO 1
<211> LENGTH: 20
<212> TYPE: PRT
<213> ORGANISM: homo sapien

<400> SEQUENCE: 1

Met Asp Tyr Gln Val Ser Ser Pro Ile Tyr Asp Ile Asn Tyr Tyr Thr
1               5                   10                  15

Ser Glu Pro Cys
            20

<210> SEQ ID NO 2
<211> LENGTH: 15

```
<212> TYPE: PRT
<213> ORGANISM: homo sapien

<400> SEQUENCE: 2

His Tyr Ala Ala Ala Gln Trp Asp Phe Gly Asn Thr Met Cys Gln
 1               5                  10                  15

<210> SEQ ID NO 3
<211> LENGTH: 20
<212> TYPE: PRT
<213> ORGANISM: homo sapien

<400> SEQUENCE: 3

Cys Ser Ser His Phe Pro Tyr Ser Gln Tyr Gln Phe Trp Lys Asn Phe
 1               5                  10                  15

Gln Thr Leu Lys
         20

<210> SEQ ID NO 4
<211> LENGTH: 21
<212> TYPE: PRT
<213> ORGANISM: homo sapien

<400> SEQUENCE: 4

Asp Ile Asn Tyr Tyr Thr Ser Glu Pro Cys Gln Lys Ile Asn Val Lys
 1               5                  10                  15

Gln Ile Ala Ala Arg
         20

<210> SEQ ID NO 5
<211> LENGTH: 20
<212> TYPE: PRT
<213> ORGANISM: homo sapien

<400> SEQUENCE: 5

Arg Ser Gln Lys Glu Gly Leu His Tyr Thr Cys Ser Ser His Phe Pro
 1               5                  10                  15

Tyr Ser Gln Tyr
         20

<210> SEQ ID NO 6
<211> LENGTH: 20
<212> TYPE: PRT
<213> ORGANISM: homo sapien

<400> SEQUENCE: 6

Asn Thr Phe Gln Glu Phe Phe Gly Leu Asn Asn Cys Ser Ser Ser Asn
 1               5                  10                  15

Arg Leu Asp Gln
         20

<210> SEQ ID NO 7
<211> LENGTH: 20
<212> TYPE: PRT
<213> ORGANISM: homo sapien

<400> SEQUENCE: 7

Met Asp Tyr Gln Val Ser Ser Pro Ile Tyr Asp Ile Asp Tyr Tyr Thr
 1               5                  10                  15

Ser Glu Pro Cys
         20
```